(12) United States Patent
Welch et al.

(10) Patent No.: US 6,787,646 B1
(45) Date of Patent: Sep. 7, 2004

(54) TUMOR SUPPRESSOR MOLECULES AND METHODS OF USE

(75) Inventors: Peter J. Welch, San Diego, CA (US); Jack R. Barber, San Diego, CA (US)

(73) Assignee: Immusol, Inc., San Diego, CA (US)

(*) Notice: Subject to any disclaimer, the term of this patent is extended or adjusted under 35 U.S.C. 154(b) by 0 days.

(21) Appl. No.: 09/438,917

(22) Filed: Nov. 12, 1999

(51) Int. Cl.$^7$ .......................... C07H 21/04; C07H 1/00; C07H 5/04; C07H 5/06; C07H 37/00
(52) U.S. Cl. .................. 536/23.5; 536/1.11; 536/18.7; 536/22.1; 536/23.1; 530/300; 530/350
(58) Field of Search .............................. 536/23.1, 1.11, 536/18.7, 22.1, 23.8, 2; 530/300, 350

(56) References Cited

U.S. PATENT DOCUMENTS 5,821,118 A * 10/1998 Omer et al.

FOREIGN PATENT DOCUMENTS

| WO | WO 97/46675 | * 11/1997 |
| WO | WO/98 32880 | 7/1998 |
| WO | WO 99/02675 | * 1/1999 |
| WO | WO/99 53031 | 10/1999 |
| WO | WO/00 05415 | 2/2000 |
| WO | WO/00 15799 | 3/2000 |

OTHER PUBLICATIONS

Lazar et al. Transforming Growth Factor alpha: Mutation of Aspartic Acid 47 and Leucine 48 Results in Different Biological Activities. Molecular and Cellular Biology 8(3): 1247–12552, Mar. 1988.*
Malkin, D. The role of p53 in human cancer. J. Neurooncol. 51(3): 231–243, Feb. 2001.*
GenCore, nucleic acid database sheets for U.S. Pat. No. 5,821,118 disclosing SEQ ID No: 2 and SEQ ID No: 18, two sheets, Oct. 13, 1998.*
GenCore, nucleic acid database sheets for WO 97/46675, Accession No. AAV10266, two sheets, Jun. 3, 1998.*
GenCore, nucleic acid database sheets for WO 99/02675, Accession No. AAX07369, four sheets, Jun. 7, 1999.*
GENBANK AA495929 (Jun. 30, 1997).
GENBANK AA583557 (Sep. 5, 1997).
GENBANK AI247609 (Nov. 4, 1998).
GENBANK AB016160 (Jan. 22, 1999).
GENBANK AF030453 (Nov. 24, 1998).
GENBANK AB016161 (Jan. 22, 1999).
GENBANK AC003104 (Jun. 25, 1998).
GENBANK AI078456 (Aug. 10, 1998).
GENBANK Z54280 (Jan. 15, 1997).
GENBANK AI084732 (Aug. 17, 1998).
GENBANK AC005739 (Oct. 1, 1998).
GENBANK AI147476 (Sep. 29, 1998).
GENBANK X68128 (Jun. 1, 1994).
GENBANK C73064 (Sep. 22, 1997).
GENBANK Z98755 (Nov. 23, 1999).
GENBANK D24303 (Dec. 2, 1993).
GENBANK R12420 (Apr. 12, 1995).
GENBANK D42474 (May 4, 1998).
GENBANK AI359294 (Jan. 6, 1999).
GENBANK D46041 (Mar. 9, 1995).
GENBANK AC006022 (Dec. 21, 1999).
GENBANK H28699 (Jul. 14, 1995).
GENBANK AB014571 (Feb. 6, 1999).
GENBANK T92983 (Mar. 22, 1995).
GENBANK AA406194 (May 1, 1997).
GENBANK W84786 (Sep. 6, 1996).
GENBANK AA278399 (Apr. 2, 1997).
GENBANK W84833 (Sep. 6, 1996).
GENBANK AI147481 (Sep. 29, 1998).
GENBANK AA211219 (Jan. 16, 1997).
GENBANK L00634 (Jun. 12, 1993).
GENBANK AA571392 (Aug. 27, 1997).
GENBANK L10413 (Jan. 30, 1996).
GENBANK AA160809 (Jun. 24, 1997).
GENBANK D29973 (Feb. 7, 1999).
GENBANK S69381 (Sep. 23, 1994).
GENBANK AA511830 (Jul. 8, 1997).
GENBANK Z82189 (Dec. 12, 1999).
GENBANK AA474138 (Jun. 18, 1997).
GENBANK AC005165 (Jun. 20, 1998).
GENBANK C85533 (Mar. 2, 1998).
GENBANK AA408534 (May 2, 1997).
GENBANK AA408064 (May 2, 1997).
GENBANK C87343 (Mar. 2, 1998).
GENBANK AI326830 (Dec. 23, 1998).
GENBANK AA070605 (Oct. 27, 1997).
GENBANK AA655540 (Nov. 4, 1997).
GENBANK AC003957 (Dec. 29, 1997).
GENBANK AC003695 (Oct. 29, 1998).
GENBANK U09941 (Mar. 14, 1995).
GENBANK AC002091 (May 13, 1997).
GENBANK X64080 (Dec. 15, 1997).
GENBANK X98523 (Oct. 30, 1996).
GENBANK D26094 (Dec. 3, 1993).
GENBANK AJ011930 (Nov. 11, 1998).
GENBANK Y00057 (Jul. 28, 1995).
GENBANK AC005668 (Sep. 10, 1998).
GENBANK M15395 (Jan. 6, 1995).

(List continued on next page.)

Primary Examiner—Alana M. Harris
(74) Attorney, Agent, or Firm—Foley & Lardner LLP

(57) ABSTRACT

The invention provides substantially pure tumor suppressor nucleic acid molecules and tumor suppressor polypeptides. The invention also provides hairpin ribozymes and antibodies selective for these tumor suppressor molecules. Also provided are methods of detecting a neoplastic cell in a sample using detectable agents specific for the tumor suppressor nucleic acids and polypeptides.

3 Claims, 8 Drawing Sheets

OTHER PUBLICATIONS

GENBANK U94776 (Jun. 1, 1998).
GENBANK AA158729 (Jun. 24, 1997).
GENBANK AA357439 (Apr. 21, 1997).
GENBANK AA600873 (Sep. 23, 1997).
GENBANK W87345 (Jun. 24, 1996).
GENBANK AB000909 (Apr. 7, 1998).
GENBANK AA492602 (Jun. 25, 1997).
GENBANK AF067845 (Feb. 8, 1999).
GENBANK AI325663 (Dec. 23, 1998).
GENBANK AA575760 (Sep. 21, 1997).
GenBank Accession No.: AF102805, Mar. 3, 1999.
GenBank Accession No.: AF043700, Jan. 22, 1998.
GenBank Accession No.: AAD16459, Dec. 21, 1999.
GenBank Accession No.: Z98531, Jul. 7, 1999.
GenBank Accession No.: Q12153, Jul. 15, 1998.
GenBank Accession No.: P38789, Nov. 1, 1997.
Boylan et al., "Activation of Tumor Suppressor Genes in Nontumorigenic Revertants of the HeLa Cervical Carcinoma Cell Line," *Cell Growth Differentiation* 7:725–735 (1996).

Migeon et al., Cloning and Characterization of peter pan, a Novel Drosophila Gene Required for Larval Growth, *Mol. Biol. Cell.* 10:1733–1744 (1999).

Ahn, et al., "Identification of cDNAs for Sox–4, an HMG–box protein, and a noval human homolog of yeast splicing factor SSF–1 differentially regulated during apoptosis induced by prostaglandin Az/delta12–PGJ2 in Hep3B cells," *Biochemical and Biophysical Research Communications, 260*:216–221 (1999).

Nylandsted, et al., "Expression of a p16INK4a–specific ribozyme downmodulates p16INK4a abundance and accelerates cell proliferation," *FEBS Letters, 436*(1):41–45 (1998).

Suarez–Huerta, et al., "Cloning, genomic organization, and tissue distribution of human Ssf–1," *Biochemican and Biophysical Research Communications, 275*:37–42 (2000).

Welch, et al., "Identification and validation of a gene involved in anchorage–independent cell growth control using a library of randomized hairpin ribozymes," *Genomics, 66*:274–283 (2000).

* cited by examiner

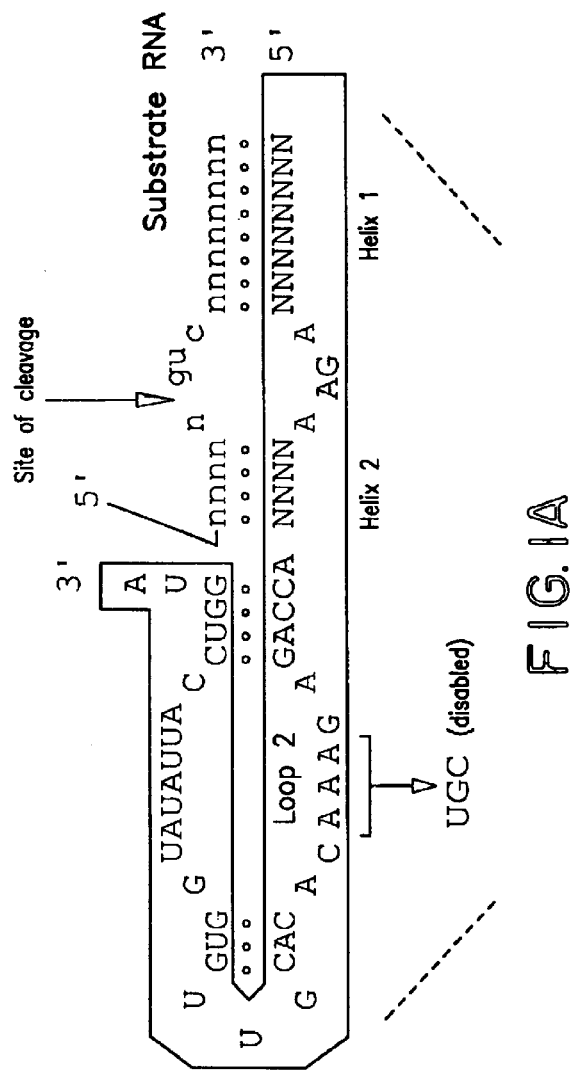
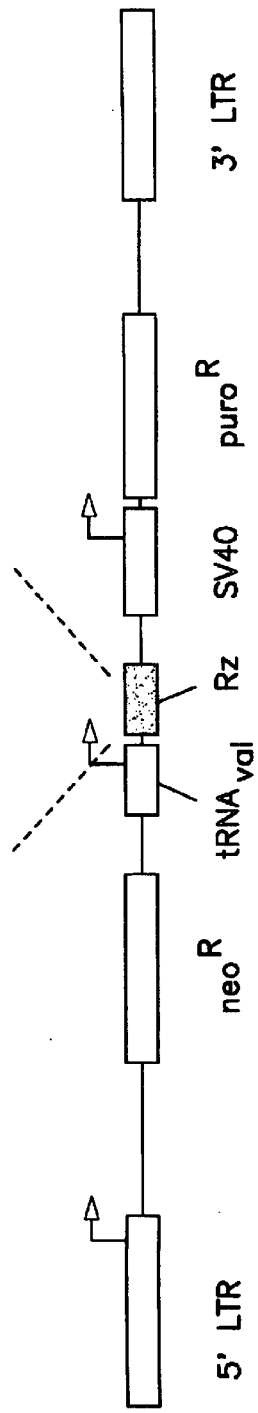
FIG. 1A
FIG. 1B

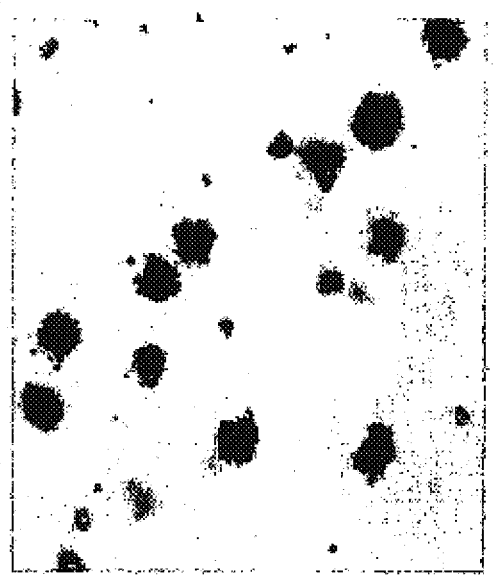
Fig. 2A — Hela
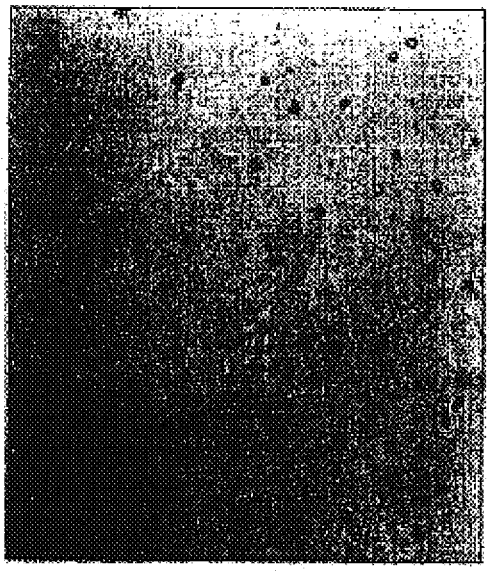
Fig. 2B — HF
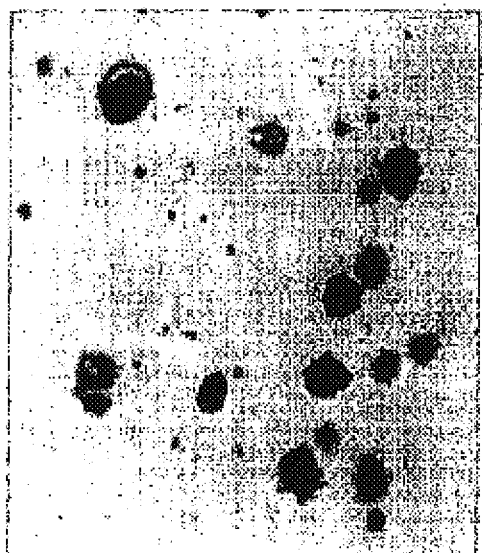
Fig. 2C — HF-568
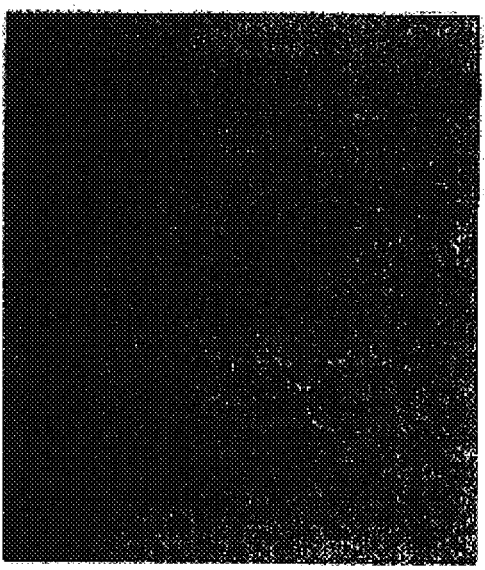
Fig. 2D — HF-d568

| | | | | | | |
|---|---|---|---|---|---|---|
| Hs | MGQSGRSRHQ | KFAPHQAQLR | NLEAYAANPH | SFVFTRGCTG | RNIRQLSLDV | 50 |
| Mm | MGQSGRSRHQ | KRNRAQAQLR | NLESYAAQPH | SFVFTRGRAG | RNVRQLSLDV | 50 |
| Dm | MGG-KKKVHP | KTRTAAFKAS | EPSEIVEAPH | SFVIHRGLAC | PYDTDLTLDF | 49 |
| | | | | | | |
| Hs | RRVMEPVTAS | RLQVRKKNSL | KDCVAVAGPL | GVTHFLILAK | QEDNVYFKLM | 100 |
| Mm | RRVMEPITAT | RLQVRKKNSL | KDCVAVAGPL | GVTHFLILTK | TCNSVYLKLM | 100 |
| Dm | RRIMEPFTAS | NLREKRMNRI | QDFVCLSSFF | HVSHMGIFNK | ASTQLSFKVV | 99 |
| | | | | | | |
| Hs | RLPGGPTLTF | QVKKYSLMRD | VVSSLRRHRM | HEQQFAHPPL | LVLNSFGPHG | 150 |
| Mm | RLPGGPTLTF | QISKYTLIRD | VVSSLRRHRM | HEQQFNHPPL | LVLNSFGPQA | 150 |
| Dm | RLHRGESLTF | KVHQFTLARD | MISLSKKQMI | CNCHFKHAPL | VIMNNESGDE | 149 |
| | | | | | | |
| Hs | MHVKLMATMF | QNLFPSINVH | KVNLNTIKRC | LLIDYNPDSQ | ELDFRHYSIK | 200 |
| Mm | MHIKLMATMF | QNLFPSINVH | TVNLNTIKRC | LLINYNPDSQ | ELDFRHYSVK | 200 |
| Dm | KHLKLMATTE | QNMFPSINLA | TVNIGTIRRC | VLFSYNPDTK | LVEMRHYSVQ | 199 |
| | | | | | | |
| Hs | VVPVGASRGM | KKLLQEKFPN | MSRLQDISEL | LATGAGLSES | EAEPDGDHNI | 250 |
| Mm | VVPVGASRGM | KKLLQEKFPN | MSRLQDISEL | LATGVGLSDS | EVEPDGEHNT | 250 |
| Dm | VVPVGLKRAV | QKIVKGTVPN | LGKCNEVVDF | VTKDGYASES | EAEDDEQSHV | 249 |
| | | | | | | |
| Hs | TELPQAVAGR | GNMRAQQSAV | RLTEIGPRMT | LQLIKMQEGV | GEGKMMFHSF | 300 |
| Mm | TELPQAVAGR | GNMAQQSAV | RLTEIGPRMT | LQLIKIQEGV | GNGNVLFHSF | 300 |
| Dm | V-LAQTLKSK | GNLEDKKSSI | KLHEIGPRID | MQLIKIFEGL | LTGEVLYHDH | 298 |
| | | | | | | |
| Hs | VSKTEEELQA | ILAAKEKKLR | LKAQRQAQQA | QNVQFKQEQR | EAHRKKSLEG | 350 |
| Mm | VHKTEEELQA | ILAAKEEKLR | LKAQRQNQQA | ENIQFSRSCR | GPQEEEP--G | 348 |
| Dm | VMKTEDEKET | LRKLVEKKRK | QKEQRKKEQA | ENRAKNLKLK | KDEKWAAKRA | 348 |
| | | | | | | |
| Hs | MKKARVGGSD | EEAS-GIPSR | TASLELGECD | DRQFLDDLEY | FCQAVGEAPS | 399 |
| Mm | RHKASPCKGR | RZQZCZGERG | TARGQWGAGQ | PEDEEDDAEY | FRQAVGEEPD | 398 |
| Dm | AEGRTDS--- | ---------- | ---------- | --DPEDDAEY | YKEEVGEEPD | 373 |
| | | | | | | |
| Hs | EDLFH-EAKQ | KRLAKSPG-- | --RKRKRWEM | D-RGRGRLCD | --QFFPKT-- | 439 |
| Mm | EDLFHTAAKR | RR----QGGL | LAKK------ | Q-RGKEQRPG | NK | 437 |
| Dm | EELFKMEAKS | SRKRPSLGGG | MKYKNKRAKL | DTKDKNCKSE | RTDFYDRKCK | 423 |
| | | | | | | |
| Hs | ---KDKSQGA | QARRGPRGAS | RDGGRGRGRG | RPGKRVA | | 473 |
| Dm | FDRKDKKDKF | DPKNGRAKFD | PKNKRAKFDH | EKSRK-SK | | 460 |

FIG. 3B

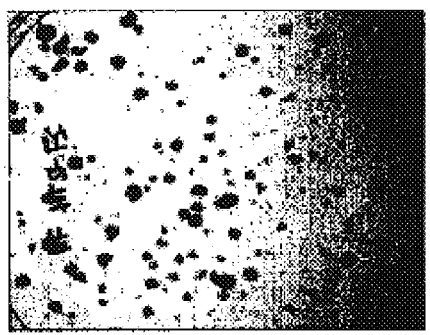
Fig. 5A — HF Vector
Fig. 5B — HeLa Vector
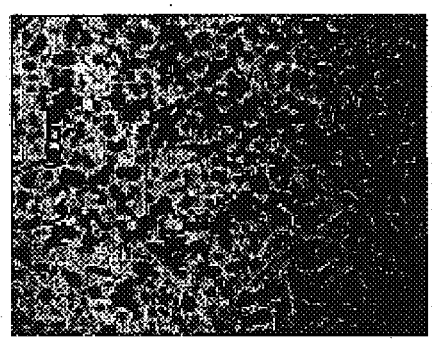
Fig. 5C — HF hPPAN
Fig. 5D — HeLa hPPAN
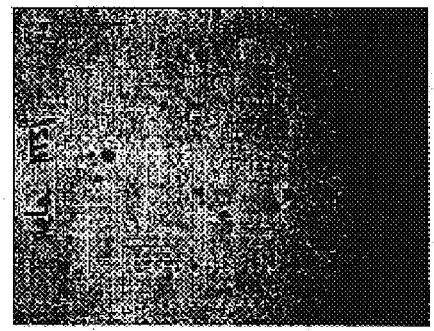
Fig. 5E — HF FS
Fig. 5F — HeLa FS
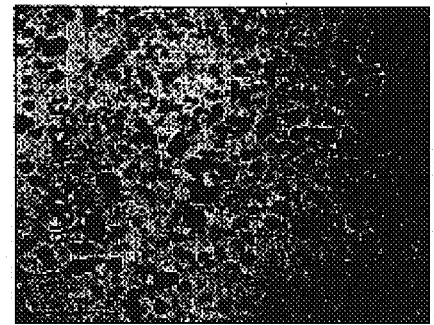

```
        |   10       |   20       |   30       |   40       |   50       |   60
    1   GCCTGATGTC   GTCCCACGCC   GTGCCGGCTC   TCAGGCGCCG   GAAGTGAGCT   GCGCACGGCC    60
   61   GGAAGCGGCG   GACGCAGGAG   GCCTCGTGGA   GGACACAGCA   GCATGGGACA   GTCAGGGAGG   120
  121   TCCCGGCACC   AGAAGCGCGC   CCCGCCCCAG   GCGCAGCTCC   GCAACCTCGA   GGCCTATGCC   180
  181   GCGAACCCGC   ACTCGTTCGT   GTTCACGCGA   GGCTGCACGG   GTCGCAACAT   CCGGCAGCTC   240
  241   AGCCTGGACG   TGCGGCGGGT   CATGGAGCCC   GTCACTGCCA   GCCGTCTGCA   GGTTCGTAAG   300
  301   AAGAACTCGC   TGAAGGACTG   CGTGGCAGTG   GCTGGGCCCC   TCGGGGTCAC   ACACTTTCTG   360
  361   ATCCTAGCAA   AACAAGAGAC   CAATGTCTAC   TTTAAGCTGA   TGCGCCTCCC   AGGAGGCCCC   420
  421   ACCTTGACCT   TCCAGGTCAA   GAAGTACTCG   CTGGTGCGTG   ATGTGGTCTC   CTCACTGCGC   480
  481   CGGCACCGCA   TGCACGAGCA   GCAGTTTGCC   CACCCACCCC   TCCTGGTACT   CAACAGCTTT   540
  541   GGCCCCCATG   GTATGCATGT   GAAGCTCATG   GCCACCATGT   TCCAGAACCT   GTTCCCCTCC   600
  601   ATCAACGTGC   ACGGGTGAA   CCTGAACACC   GCCTCCTCAT   CGACTACAAC   660
  661   CCCGACTCCC   AGGAGCTGGA   CTTCCGCCAC   TATAGCATCA   AGGTTGTTCC   TGTGGGCGCG   720
  721   AGTCGCGGGA   TGAAGAAGCT   GCTCCAGGAG   AAGTTCCCCA   ACATGAGCCG   CCTGCAGGAC   780
  781   ATCAGCGAGC   TGCTGGCCAC   GGGCGCGGGG   CTGTCGGAGA   GCGAGGCAGA   GCCTGACGGC   840
  841   GACCACAACA   TCACAGAGCT   GCCTCAGGCT   GTCGCTGGCC   GTGGCAACAT   GCGGGCCCAG   900
  901   CAGAGTGCAG   TGCGGCTCAC   CGAGATCGGC   CCGCGGATGA   CACTGCAGCT   CATCAAGGTC   960
  961   CAGGAGGGCG   TCGGGGAGGG   CAAAGTGATG   TTCCACAGTT   TTGTGAGCAA   GACGGAGGAG  1020
 1021   GAGCTGCAGG   CCATCCTGGA   AGCCAAGGAG   AAGAAGCTGC   GGCTGAAGGC   TCAGAGGCAG  1080
 1081   GCCCAGCAGG   CCCAGAATGT   GCAGCGCAAG   CAGGAGCAGC   GGGAGGCCCA   CAGAAAGAAG  1140
 1141   AGCCTGGAGG   GCATGAAGAA   GGCACGGGTC   GGGGGTAGTG   ATGAAGAGGC   CTCTGGGATC  1200
 1201   CCTTCAAGGA   CGGCGAGCCT   GGAGTTGGGT   GAGGACGATG   ATGAACAGGA   AGATGATGAC  1260
 1261   ATCGAGTATT   TCTGCCAGGC   GGTGGGCGAG   GCGCCCAGTG   AGGACCTGTT   CCCCGAGGCC  1320
 1321   AAGCAGAAAC   GGCTTGCCAA   GTCTCCAGGG   CGGAAGCGGA   AGCGGTGGGA   AATGGATCGA  1380
 1381   GGCAGGGGTC   GCCTTTGTGA   CCAGAAGTTT   CCCAAGACCA   AGGACAAGTC   CCAGGGAGCC  1440
 1441   CAGGCCAGGC   GGGGGCCCAG   AGGGGCTTCC   CGGGATGGTG   GGCGAGGCCG   GGGCCGAGGC  1500
 1501   CGCCCAGGGA   AGAGAGTGGC   CTGAGCCCAA   GCCGCACCGG   AGCAGCGGCT   GGATTGAACG  1560
 1561   CCCCAGATTG   GGGCCCGAGA   TGTGGCCCTC   GGTTTCCTTT   CATAAAGGAG   TTGTGTCCCC  1620
 1621   AGCCCTTCCA   CTCCAGTAAA   GAACTGAATT   GGCAAAAAAA   AAAA                     1664
        |   10       |   20       |   30       |   40       |   50       |   60
```

FIG. 6A

```
        |   10        |   20        |   30        |   40        |   50        |   60
    1   MGQSGRSRHQ    KRAPPQAQLR    NLEAYAANPH    SFVFTRGCTG    RNIRQLSLDV    RRVMEPVTAS    60
   61   RLQVRKKNSL    KDCVAVAGPL    GVTHFLILAK    QETNVYFKLM    RLPGGPTLTF    QVKKYSLVRD   120
  121   VVSSLRRHRM    HEQQFAHPPL    LVLNSFGPHG    MHVKLMATMF    QNLFPSINVH    KVNLNTIKRC   180
  181   LLIDYNPDSQ    ELDFRHYSIK    VVPVGASRGM    KKLLQEKFPN    MSRLQDISEL    LATGAGLSES   240
  241   EAEPDGDHNI    TELPQAVAGR    GNMRAQQSAV    RLTEIGPRMT    LQLIKVQEGV    GEGKVMFHSF   300
  301   VSKTEEELQA    ILEAKEKKLR    LKAQRQAQQA    QNVQRKQEQR    EAHRKKSLEG    MKKARVGGSD   360
  361   EEASGIPSRT    ASLELGEDDD    EQEDDDIEYF    CQAVGEAPSE    DLFPEAKQKR    LAKSPGRKRK   420
  421   RWEMDRGRGR    LCDQKFPKTK    DKSQGAQARR    GPRGASRDGG    RGRGRGRPGK    RVAZ         474
        |   10        |   20        |   30        |   40        |   50        |   60
```

FIG. 6B

```
MM      FGQGGKQAAWGSPGGPDIRSAIAPGELRNLESYAAQPHSFV  41
HS

MM      FTRG---RAGRNVRQLSLDVRRVMEPLTATRLQVRKKNSLKDCVAVAGPLGVTMFLILTK  98
HS                                            LGPRVTMFLDLSK  13

MM      TD--NSVYLKLMRLPGGPTLTFQISKYTLIRDVVSSLRRH-RMHEQQFNHPPLLVLNSFG  155
HS      TE--DNVYFKLMRLPGGPTLTFQVKKYSLVRDVVSSLRRH-RMHEQQFAMPPLLVLNSFG  70

MM      PQG---------MMIKLMATMFQNLFPSINVHTVNLNTJKRGLLINYNPD-SQELDFRHY  205
HS      PHG---------MMVKLMATMFQNLFPSINVHKVNLNTJKRCSSXDLKPGFPRSLDFRPI  121

MM      SVKVVPVGASRGMKKLLQ------EKFPNMSRLQDISELLATGVG-----------  244
HS      IAFKGGSCWAPNSGGL                                           137

MM      ----------------LSDSEVEPDGEHN------TTELPQAVAG-RGNMQAQQSA  277

MM      VRLTEIGPRMILQLIKIQEGVGNGNVLFMSFVHKTEEELQAILAAKEEKLRLKADRQNQD  337

MM      AENLQRXRSCRXPTRRRAWQA---------------  358
```

TUMOR SUPPRESSOR MOLECULES AND METHODS OF USE

STATEMENT AS TO FEDERALLY-FUNDED RESEARCH

This invention was supported by government support under contract number DE-FG03-98ER62624 awarded by the United States Department of Energy. The government has certain rights in this invention.

BACKGROUND OF THE INVENTION

This invention relates generally to proliferative diseases such as cancer and, more specifically, to tumor suppressor molecules that can be used to diagnose and treat proliferative diseases.

Cancer is one of the leading causes of death in the United States. Each year, more than half a million Americans die from cancer, and more than one million are newly diagnosed with the disease. Cancerous tumors result when a cell escapes from its normal growth regulatory mechanisms and proliferates in an uncontrolled fashion. Tumor cells can metastasize to secondary sites if treatment of the primary tumor is either not complete or not initiated before substantial progression of the disease. Early diagnosis and effective treatment of tumors is therefore essential for survival.

Cancer involves the clonal replication of populations of cells that have gained competitive advantage over normal cells through the alteration of regulatory genes. Regulatory genes can be broadly classified into "oncogenes" which, when activated or overexpressed promote unregulated cell proliferation, and "tumor suppressor genes" which, when inactivated or underexpressed fail to prevent abnormal cell proliferation. Loss of function or inactivation of tumor suppressor genes is thought to play a central role in the initiation and progression of a significant number of human cancers.

A number of tumor suppressor genes have been identified that, when inactivated, are involved in the initiation or progression of human cancers. Known tumor suppressor genes include, for example, RB, p53, DCC, APC/MCC, NF1, NF2, WT1, VHL, BRCA1, MST1 and WAF1/CIP1. Approaches for treating cancer by modulating the function of certain of these tumor suppressor genes, either with pharmaceutical compounds or by gene therapy methods, have yielded promising results in animal models and in human clinical trials.

Approaches for diagnosing and prognosing cancer by identifying mutations in known tumor suppressor genes have also been developed. For example, identifying individuals containing germline mutations in known tumor suppressor genes has permitted the identification of individuals at increased risk of developing cancer. Such individuals are then closely monitored or treated prophylactically to improve their chance of survival. Identifying the pattern of alterations of known tumor suppressor genes in biopsy samples is also being used to determine the presence or stage of a tumor. Being able to determine whether a cancer is benign or malignant, at an early or late stage of progression, provides the patient and clinician with a more accurate prognosis and can be used to determine the most effective treatment.

In view of the importance of tumor suppressor molecules in the detection and treatment of cancer, there exists a need to identify additional tumor suppressor nucleic acids and polypeptides. The present invention satisfies this need and provides related advantages as well.

SUMMARY OF INVENTION

The invention provides substantially pure tumor suppressor nucleic acid molecules. In one embodiment, the invention provides a substantially pure tumor suppressor nucleic acid molecule having at least fifteen contiguous nucleotides of SEQ ID NO:2, or a functional fragment thereof. In another embodiment, the invention provides a substantially pure nucleic acid molecule having substantially the same nucleic acid sequence as SEQ ID NO:5, or a functional fragment thereof. In yet another embodiment, the invention provides a substantially pure tumor suppressor nucleic acid molecule having at least fifteen contiguous nucleotides of SEQ ID NO:4, or a functional fragment thereof.

The invention also provides substantially pure hairpin ribozyme nucleic acid molecules, containing a sequence selected from the group consisting of SEQ ID NO:1 and SEQ ID NO:3.

The invention further provides a substantially pure tumor suppressor polypeptide having substantially the same amino acid sequence as SEQ ID NO:6, or a functional fragment thereof. A substantially pure antibody or antigen binding fragment reactive with the tumor suppressor polypeptide is also provided.

Also provided are methods of detecting a neoplastic cell in a sample. In one embodiment, the method consists of contacting the sample with a detectable agent specific for a tumor suppressor nucleic acid of the invention and detecting the nucleic acid molecule in the sample, wherein altered expression or structure of the nucleic acid molecule indicates the presence of a neoplastic cell in said sample. In another embodiment, the method consists of contacting the sample with a detectable agent specific for a tumor suppressor polypeptide of the invention and detecting the polypeptide in the sample, wherein altered expression or structure of the polypeptide indicates the presence of a neoplastic cell in the sample.

BRIEF DESCRIPTION OF THE DRAWINGS

FIG. 1A shows the general structure and nucleotide sequence of a hairpin ribozyme (SEQ ID NO:10) and its interaction with a substrate RNA. FIG. 1B shows the pLHPM retroviral vector used to clone the ribozyme gene library.

FIGS. 2A, 2B, 2C and 2D, respectively, show soft agar colony formation in HF cells; HF cells prior to transfection with ribozyme; HF cells stably transfected with ribozyme 568 (Rz 568), and HF cells stably transfected with disabled ribozyme (d568), after two rounds of soft agar selection.

FIG. 3B shows an alignment of HTS1 (Hs) amino acid sequence with PPAN sequences from Drosophila (Dm) (SEQ ID NO:17) and deduced from Mouse (Mm) (SEQ ID NO:16).

FIG. 5 shows colonies of Hela and HF cells formed after transfecting cells with vector control (5A and 5B), with HTS1 (hPPAN) (5C and 5D), and with a frameshift mutant (FS) (5E and 5F), followed by two weeks of hygromycin selection.

FIG. 6A shows the nucleotide sequence (SEQ ID NO:5) and FIG. 6B shows the amino acid sequence (SEQ ID NO:6) of the human tumor suppressor molecule designated HTS1.

FIG. 7 shows a deduced partial amino acid sequence of mouse PPAN (MM; SEQ ID NO:19) and human PPAN (HS; SEQ ID NO:20) compiled from ESTs, as set forth in FIG. 4 of Migeon et al., *Mol. Biol. Cell.* 10:1733–1744 (1999).

DETAILED DESCRIPTION OF THE INVENTION

Figure 3A:
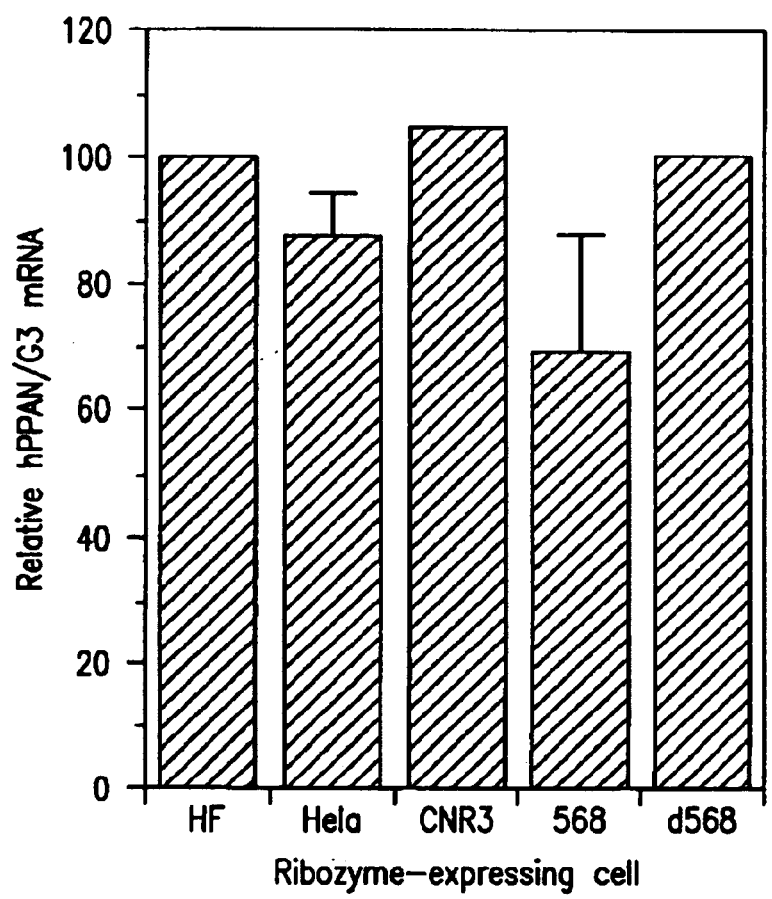
FIG. 3A shows the relative level of HTS1 (hPPAN) mRNA in HF parental cells, Hela cells, and HF cells expressing either CNR3 (control), 568 or d568 ribozymes.

The present invention provides novel tumor suppressor molecules, including tumor suppressor nucleic acids and polypeptides. The tumor suppressor molecules of the invention can be used to detect neoplastic cells in a sample and, therefore, to diagnose and prognose cancer. The tumor suppressor molecules of the invention can also be introduced into neoplastic cells to regulate cell proliferation and, therefore, are useful as therapeutics for treating cancer. Furthermore, the tumor suppressor molecules of the invention can be used to identify compounds that mimic or regulate their tumor suppressor activity. Such compounds can be used as therapeutics to treat cancer.

As used herein, the term "tumor suppressor" when used in reference to a nucleic acid molecule or polypeptide is intended to mean either a nucleic acid molecule, or an encoded polypeptide which, when functionally inactivated in a cell, promotes unregulated cell proliferation. As described herein, one method of functionally inactivating a tumor suppressor nucleic acid molecule in a cell is by introducing into the cell a gene for a hairpin ribozyme with specificity for the tumor suppressor nucleic acid molecule. The hairpin riboyzme, binds the specific target site in the cellular mRNA and cleaves the transcript, preventing the expression of a functional tumor suppressor polypeptide. Those skilled in the art will appreciate that expression of an active tumor suppressor molecule in a cell, particularly in a cell in which the endogenous tumor suppressor molecule has been functionally inactivated, can confer, to some extent, normal regulatory properties on the cell.

As used herein, the term "substantially pure," in regard to a nucleic acid molecule or polypeptide of the invention, is intended to mean a molecule that is substantially free from cellular components or other contaminants that are not the desired molecule. A substantially pure nucleic acid molecule or polypeptide will generally resolve as a major band by gel electrophoresis, and will generate a nucleotide or amino acid sequence profile consistent with a predominant species.

As used herein, the term "nucleic acid molecule" is intended to mean a single- or double-stranded DNA or RNA molecule. Thus, a nucleotide designated as "T" is equivalent to a "U" nucleotide in a recited sequence. The term is intended to include nucleic acid molecules of both synthetic and natural origin. A nucleic acid molecule of natural origin can be derived from any animal, such as a human, non-human primate, mouse, rat, rabbit, bovine, porcine, ovine, canine, feline, or amphibian. A nucleic acid molecule of the invention can be of linear, circular or branched configuration, and can represent either the sense or antisense strand, or both, of a native nucleic acid molecule. A nucleic acid molecule of the invention can further incorporate a detectable moiety such as a radiolabel, a fluorochrome, a ferromagnetic substance, a luminescent tag or a detectable binding agent such as biotin, when used in a diagnostic method described herein. Additionally, a nucleic acid molecule of the invention can include one or more non-native nucleotides, having, for example, modifications to the base, the sugar, or the phosphate portion, or having a modified phosphodiester linkage. Such modifications can be advantageous in increasing the stability of the nucleic acid molecule.

As used herein, the term "functional fragment," in regard to a nucleic acid molecule of the invention refers to a portion of the nucleic acid molecule having the ability to selectively hybridize with the subject nucleic acid molecule. The term "selectively hybridize" refers to an ability to bind the subject nucleic acid molecule without substantial cross-reactivity with a molecule that is not the subject nucleic acid molecule. Thus, a functional fragment of a nucleic acid molecule of the invention can be used, for example, as a PCR primer to selectively amplify a nucleic acid molecule of the invention; as a selective primer for 5' or 3' RACE to determine additional 5' or 3' sequence of a nucleic acid molecule of the invention; as a selective probe to identify or isolate a nucleic acid molecule of the invention on a Northern or Southern blot, or genomic or cDNA library; or as a selective inhibitor of transcription or translation of a tumor suppressor nucleic acid in a cell or cell extract.

A functional fragment of a nucleic acid molecule of the invention includes at least 15 contiguous nucleotides from the reference nucleic acid molecule, can include at least 16, 17, 18, 19, 20 or at least 25 nucleotides, often includes at least 30, 40, 50, 75, 100, 200, 300, 400, 500, 600, 800, 1000 nucleotides, and can include up to the full length of the reference nucleic acid molecule minus one nucleotide. Functional fragments of such lengths are able to selectively hybridize with the subject nucleic acid molecule in a variety of detection formats described herein.

As used herein, the term "substantially the same nucleotide sequence" in reference to a nucleic acid molecule of the invention or a fragment thereof includes sequences having one or more additions, deletions or substitutions with respect to the reference sequence, so long as the nucleic acid molecule retains its ability to selectively hybridize with the subject nucleic acid molecule under moderately stringent conditions, or highly stringent conditions. The term "moderately stringent conditions," as used herein, refers to hybridization conditions equivalent to hybridization of filter-bound nucleic acid in 50% formamide, 5× Denhart's solution, 5×SSPE, 0.2% SDS at 42° C., followed by washing in 0.2×SSPE, 0.2% SDS, at 50°. As used herein, "highly stringent conditions" are conditions equivalent to hybridization of filter-bound nucleic acid in 50% formamide, 5× Denhart's solution, 5×SSPE, 0.2% SDS at 42° C., followed by washing in 0.2×SSPE, 0.2% SDS, at 650°. Other suitable moderately stringent and highly stringent hybridization buffers and conditions are well known to those of skill in the art and are described, for example, in Sambrook et al., *Molecular Cloning; A Laboratory Manual*, Cold Spring Harbor Laboratory, New York (1992) and in Ansubel et al., *Current Protocols in Molecular Biology*, John Wiley and Sons, Baltimore, Md. (1998).

In general, a nucleic acid molecule that has "substantially the same nucleotide sequence" as a reference sequence will have greater than about 60% identity, such as greater than about 65%, 70%, 75% identity with the reference sequence, such as greater than about 80%, 85%, 90%, 95%, 97% or 99% identity to the reference sequence over the length of the two sequences being compared. Identity of any two nucleic acid sequences can be determined by those skilled in the art based, for example, on a BLAST 2.0 computer alignment, using default parameters. BLAST 2.0 searching is available as described by Tatiana et al., *FEMS Microbiol Lett.* 174.247–250 (1999). The BLAST program is available online at U.S. National Cancer Institute's National Cancer Biotechnology Information ("NCBI") website.

As used herein, the term "nucleic acid molecule encoding an amino acid sequence" is intended to mean a nucleic acid molecule that encodes the reference amino acid sequence, yet can be degenerate at one or several codons with respect to the native nucleotide sequence.

As used herein, the term "substantially the same amino acid sequence" is intended to mean an amino acid sequence that contains minor modifications with respect to the reference amino acid sequence, so long as the polypeptide retains one or more of the functional activities exhibited by the polypeptide as a whole. A polypeptide that has substantially the same amino acid sequence as a reference human amino acid sequence can be, for example, a homologous polypeptide from a vertebrate species, such as a non-human primate, mouse, rat, rabbit, bovine, porcine, ovine, canine, feline, or amphibian.

A polypeptide that has substantially the same amino acid sequence as a reference sequence can also have one or more deliberately introduced modifications, such as additions, deletions or substitutions of natural or non-natural amino acids, with respect to the reference sequence. Those skilled in the art can determine appropriate modifications that, for instance, serve to increase the stability, bioavailability, bioactivity or immunogenicity of the polypeptide, or facilitate its purification, without altering the desired functional acitivity. For example, introduction of a D-amino acid or an amino acid analog, or deletion of a lysine residue, can stabilize a polypeptide and reduce degradation. Likewise, addition of tag sequeces, such as epitope or histidine tags, or sorting sequences, can facilitate purification of the recombinant polypeptide. Depending on the modification and the source of the polypeptide, the modification can be introduced into the polypeptide, or into the encoding nucleic acid sequence.

Computer programs known in the art, for example, DNASTAR software, can be used to determine which amino acid residues can be modified as indicated above without abolishing the desired functional activity. Additionally, guidance in modifying amino acid sequences while retaining functional activity is provided by aligning homologous tumor suppressor polypeptides from various species. Those skilled in the art understand that evolutionarily conserved amino acid residues and domains are more likely to play a role in the biological activity than less well-conserved residues and domains.

In general, an amino acid sequence that is substantially the same as a reference amino acid sequence will have greater than about 50% identity, preferably greater than about 60% identity, such as greater than about 70%, 75%, or about 80% identity, more preferably greater than about 85% or 90% identity, including greater than about 95%, 97% or 99% identity with the reference sequence. The amino acid sequences which align across two sequences, and the presence of gaps and non-homologous regions in the alignment, can be determined by those skilled in the art based, for example, on a BLAST 2 or Clustal W or similar computer alignment, using default parameters.

A computer alignment can, if desired, be optimized visually by those skilled in the art. The percent identity of two sequences is determined as the percentage of the total amino acids that align in such an alignment which are identical. Those skilled in the art understand that two amino acid molecules with a given percentage identity over the entire sequence or over a substantial portion or portions thereof, are more likely to exhibit similar functional activities than two molecules with the same percentage identity over a shorter portion of the sequence.

As used herein, the term "functional activity" of a polypeptide of the invention is an activity which is characteristic of the reference polypeptide. A functional activity can be, for example, immunogenicity, which is an ability to generate an antibody that selectively binds a polypeptide of the invention, or antigenicity, which is an ability to selectively compete with a polypeptide of the invention for binding to an antibody specific for a polypeptide of the invention. A "functional activity" of a tumor suppressor polypeptide of the invention can additionally or alternatively be the ability to alter, such as inhibit or promote, cell proliferation, when introduced or expressed in a cell. Such a functional activity reflects the ability of the polypeptide to either mimic or compete with the endogenous tumor suppressor polypeptide, as described below.

As used herein, the term "functional fragment" in regard to a polypeptide of the invention, refers to a portion of the reference polypeptide that is capable of exhibiting or carrying out a "functional activity" of the reference polypeptide. A functional fragment of a polypeptide of the invention exhibiting a functional activity can have, for example, at least 6 contiguous amino acid residues from the polypeptide, at least 8, 10, 15, 20, 30 or 40 amino acids, and often has at least 50, 75, 100, 200, 300, 400 or more amino acids of a polypeptide of the invention, up to the full length polypeptide minus one amino acid.

The appropriate length and amino acid sequence of a functional fragment of a polypeptide of the invention can be determined by those skilled in the art, depending on the intended use of the functional fragment. For example, a functional fragment having immunogenic or antigenic activity need only be of sufficient length to define an epitope that is specific for the polypeptide of the invention. A functional fragment that alters cell proliferation by competing with an endogenous tumor suppressor can be chosen, for example, to correspond to a portion of the polypeptide that includes the region that interacts with a substrate or regulatory molecule. A functional fragment that mimics an endogenous tumor suppressor can include, for example, an entire biologically active domain of the tumor suppressor molecule.

As used herein, the term "hairpin ribozyme" is intended to mean an RNA molecule having the general nucleic acid sequence and two-dimensional configuration of the molecule shown in FIG. 1 (SEQ ID NO:10), and which is capable of selectively binding, or of both selectively binding and cleaving, a substrate RNA. Usually, a hairpin ribozyme will have from about 50 to 54 nucleotides, and forms two helical domains (Helix 3 Helix 4) and 3 loops (Loops 2, 3 and 4). Two additional helices, Helix 1 and Helix 2, form between the ribozyme and its RNA substrate. A hairpin ribozyme binds a target RNA substrate by forming Watson-Crick base pairs between the substrate and Helix 1 and Helix 2 sequences, as shown by dots in FIG. 1, where "N" is any nucleotide, "n" is the complement of "N", "b" is generally C, G or U, and "B" is the complement of "b". The length of Helix 2 is usually 4 base pairs, and the length of Helix 1 can vary from about 6 to about 10 base pairs. A hairpin ribozyme can have catalytic activity, and thus cleave the substrate RNA at the indicated cleavage site in FIG. 1. However, the catalytic activity of the hairpin ribozyme can be disabled by altering the AAA sequence in Loop 2 to CGU, as shown in FIG. 2. Those skilled in the art can determine which modifications to the overall hairpin ribozyme structure can be made and still maintain the substrate binding, or both substrate binding and catalytic activity, of a hairpin ribozyme of the invention.

As used herein, the term "hairpin ribozyme nucleic acid molecule" includes both hairpin ribozyme RNA molecules as well as single- and double-stranded DNA molecules that, when expressed, form hairpin ribozyme RNA molecules.

As used herein, the term "specifically reactive" in relation to an HTS1 antibody or other binding compound, is intended to mean high affinity binding to HTS1 in a binding assay, such as an immunoblot or ELISA assay, without substantial cross-reactivity with other polypeptides. A specifically reactive antibody or other binding compound can have an affinity constant of greater than $10^5$ $M^{-1}$, preferably greater than $10^7$ $M^{-1}$, more preferably greater than $10^9$ $M^{-1}$, for HTS1 or a characteristic fragment therefrom.

As used herein, the term "neoplastic cell" is intended to mean a cell that has altered expression or structure of a tumor suppressor molecule of the invention compared to a normal cell from the same or a different individual. A neoplastic cell will generally also exhibit histological or proliferative features of a malignant or premalignant cell. For example, by histological methods, a neoplastic cell can be observed to invade into surrounding normal tissue, have an increased mitotic index, an increased nuclear to cytoplasmic ratio, altered deposition of extracellular matrix, or a less differentiated phenotype. A neoplastic cell can also exhibit unregulated proliferation, such as anchorage independent cell growth, proliferation in reduced-serum medium, loss of contact inhibition, or rapid proliferation compared to normal cells.

As used herein, the term "altered expression" of a nucleic acid molecule detected by a method of the invention refers to an increased or decreased amount of a tumor suppressor nucleic acid in the test sample relative to known levels in a normal sample. Altered abundance of a nucleic acid molecule can result, for example, from an altered rate of transcription, from altered transcript stability, or from altered copy number of the corresponding gene.

As used herein, the term "altered structure" of a nucleic acid molecule refers to differences, such as point mutations, deletions, translocations, splice variations and other rearrangements, between the structure of a nucleic acid molecule of the invention in a test sample and the structure of the nucleic acid molecule in a normal sample. Those skilled in the art understand that mutations that alter the structure of a nucleic acid molecule can also alter its expression.

As used herein, the term "altered expression" of a polypeptide refers to an increased or decreased amount, or altered subcellular localization, of the polypeptide in the test sample relative to known levels or localization in a normal sample. Altered abundance of a polypeptide can result, for example, from an altered rate of translation or altered copy number of the corresponding message, or from altered stability of the protein. Altered subcellular localization can result, for example, from truncation or inactivation of a sorting sequence, from fusion with another polypeptide sequence, or altered interaction with other celllular polypeptides.

As used herein, the term "altered structure" of a polypeptide refers to differences in amino acid sequence, post-translational modifications, or conformation, of the polypeptide in the test sample relative to a normal sample. Post-translational modifications include, for example, phosphorylation, glycosylation and acylation. Conformational differences include, for example, folding properties. Such differences can be detected, for example, with a structure-specific detectable binding agent.

As used herein, the term "sample" is intended to mean any biological fluid, cell, tissue, organ or portion thereof, that includes or potentially includes nucleic acids and polypeptides of the invention. The term includes samples present in an individual as well as samples obtained or derived from the individual. For example, a sample can be a histologic section of a specimen obtained by biopsy, or cells that are placed in or adapted to tissue culture. A sample further can be a subcellular fraction or extract, or a crude or substantially pure nucleic acid or protein preparation. A sample can be prepared by methods known in the art suitable for the particular format of the detection method.

As used herein, the term "detectable agent" refers to a molecule that renders a tumor suppressor molecule of the invention detectable by an analytical method. An appropriate detectable agent depends on the particular detection format, and can be determined for a particular application of the method by those skilled in the art. For example, a detetable agent specific for a tumor suppressor nucleic acid molecule can be a complementary nucleic acid molecule, such as a hybridization probe or non-catalytic ribozyme, that selectively hybridizes to the nucleic acid molecule. A hybridization probe or ribozyme can be labeled with a detectable moiety, such as a radioisotope, fluorochrome, chemiluminescent marker, biotin, or other detectable moiety known in the art that is detectable by analytical methods.

A detectable agent specific for a tumor suppressor nucleic acid molecule can also be, for example, a PCR or RT-PCR primer, which can be used to selectively amplify all or a desired portion of the nucleic acid molecule, which can then be detected by methods known in the art. Furthermore, a detectable agent specific for a tumor suppressor nucleic acid molecule can be a selective binding agent, such as a peptide, nucleic acid analog, or small organic molecule, identified, for example, by affinity screening of a library of compounds.

A detectable agent specific for a polypeptide of the invention can be, for example, an agent that selectively binds the polypeptide. For example, a detectable agent that detects a polypeptide can selectively bind with high affinity or avidity to the polypeptide, without substantial cross-reactivity with other polypeptides that are not polypeptides of the invention. The binding affinity of a detectable agent that selectively binds a polypeptide will generally be greater than about $10^{-5}$ M and more preferably greater than about $10^{-6}$ M for the polypeptide. High affinity interactions are preferred, and will generally be greater than about $10^{-8}$ M to $10^{-9}$ M.

A detectable agent specific for a polypeptide can be, for example, a polyclonal or monoclonal antibody specific for the polypeptide, or other selective binding agent identified, for example, by affinity screening of a library of compounds. For certain applications, a detectable agent can be utilized that preferentially recognizes a particular conformational or post-translationally modified state of the polypeptide. The detectable agent can be labeled with a detectable moiety, if desired, or rendered detectable by specific binding to a detectable secondary binding agent.

The invention provides a substantially pure tumor suppressor nucleic acid molecule containing at least fifteen contiguous nucleotides of the sequence set forth as SEQ ID NO:2, or a functional fragment of the tumor suppressor molecule. The invention also provides a substantially pure tumor suppressor nucleic acid molecule containing at least fifteen contiguous nucleotides of the sequence set forth as SEQ ID NO:4, or a functional fragment of the tumor suppressor molecule.

As disclosed herein, SEQ ID NO:2, 5'-AGGGNGTCGGGGAGGT-3', represents a 16-nucleotide ribozyme binding sequence of an mRNA whose cleavage by a hairpin ribozyme having the corresponding substrate binding sequence 5'-ACCTCCCCAGAACCCT-3' (SEQ ID NO:1) resulted in unregulated cell proliferation (see Example II, below). SEQ ID NO:4, 5'-TAGTNGTCTACACTCT-3', represents a 16-nucleotide ribozyme binding sequence of an mRNA whose cleavage by a hairpin ribozyme having the corresponding substrate binding sequence 5'-AGAGTGTAAGAAACTA-3' (SEQ ID NO:3) resulted in unregulated cell proliferation (see Example II, below).

Fifteen contiguous nucleotides of a ribozyme binding sequence are sufficient for specific binding and effective cleavage by the corresponding hairpin ribozyme. Therefore, a tumor suppressor nucleic acid molecule of the invention contains at least fifteen contiguous nucleotides of the sequence set forth as SEQ ID NO:2 or SEQ ID NO:4. An exemplary tumor suppressors nucleic acid molecule that contains at least fifteen contiguous nucleotides of the sequence set forth as SEQ ID NO:2 is a nucleic acid molecule containing the nucleotide sequence set forth as SEQ ID NO:18, such as a nucleic acid molecule containing the nucleotide sequence set forth as SEQ ID NO:5.

A tumor suppressor nucleic acid molecule containing at least fifteen contiguous nucleotides of SEQ ID NO:2, or a functional fragment thereof, does not consist of a nucleotide sequence having the exact endpoints of nucleotide sequences deposited in public databases at the time of filing, such as Expressed Sequence Tags (ESTs), Sequence Tagged Sites (STSs) and genomic fragments, deposited in databases such as the nr, dbest, dbsts, gss and htgs databases, which are available for searching using the program BLASTN 2.0.9 [May-07-1999] described by Altschul et al., *Nucleic Acids Res.* 25:3389–3402 (1997). The BLAST program is available online at U.S. National Cancer Institute's National Cancer Biotechnology Information ("NCBI") website.

For example, a tumor suppressor nucleic acid molecule containing at least fifteen contiguous nucleotides of SEQ ID NO:2, or a functional fragment thereof, does not consist of a nucleotide sequence having the exact endpoints of sequences having the following Accession numbers: AC006022, Z54280, AC005739, X68128, AB014571, Z98755, AF030453, AC003104, AA406194, R12420, AI247609, AA278399, AI359294, AA495929, W84833, W84786, AA583557, T92983, AI078456, AI147476, H28699, AB016161, AB016160, D46041, D42474, C73064, AI084732, D24303, AA300789, AI147481, L00634, L10413, D29973, S69381, Z82189, AC005165, AA408534, AU017817, AI326830, AA655540, AA66686, AA211219, AA571392, AA160809, AU014594, AA511830, AA474138, C85533, AA408064, C87343, AA070605, AC003957, U09941, AC003695, AC002091, X64080, X98523, AJ011930, AC005668, U94776, D26094, Y00057, M15395, AA158729, AA357439, AA600813 and W87345.

Likewise, a tumor suppressor nucleic acid molecule containing at least fifteen contiguous nucleotides of SEQ ID NO:4, or a functional fragment thereof, does not consist of a nucleotide sequence having the exact endpoints of nucleotide sequences deposited in public databases at the time of filing, such as the databases described above, including sequences having the following Accession numbers: AB000909, AF067845 and AA492602.

A tumor suppressor nucleic acid molecule of the invention containing at least fifteen contiguous nucleotides of SEQ ID NO:2 or SEQ ID NO:4 can be advantageously used, for example, as a detectable agent in the diagnostic methods of the invention, or to identify and isolate full-length tumor suppressor nucleic acid molecules by the methods disclosed herein. When used for such purposes, the nucleic acid molecule can contain none, one, or many nucleotides at the 5' or 3' end, or both, of the fifteen contiguous nucleotides. These additional nucleotides can correspond to the native sequence of the tumor suppressor nucleic acid molecule, or can be non-native sequences, or both. For example, non-native flanking sequences that correspond to a restriction endonuclease site or a tag, or which stabilize the 15-nucleotide sequence in a hybridization assay, can be advantageous when the nucleic acid molecule is used as a probe or primer to identify or isolate longer tumor suppressor nucleic acid molecules.

A tumor suppressor nucleic acid molecule of the invention containing at least fifteen contiguous nucleotides of SEQ ID NO:2 or SEQ ID NO:4, and additional sequence corresponding to a tumor suppressor nucleic acid molecule, can be used, for example, in the diagnostic and therapeutic methods disclosed herein. Native tumor suppressor nucleotide sequences flanking the fifteen contiguous nucleotides of SEQ ID NO:2 or SEQ ID NO:4 can be determined by methods known in the art, such as RT-PCR, 5' or 3' RACE, screening of cDNA or genomic libraries, and the like, using an oligonucleotide having fifteen contiguous nucleotides of SEQ ID NO:2 of SEQ ID NO:4 as a primer or probe, and sequencing the resultant product (see Example III, below). The appropriate source of template RNA or DNA for amplification, extension or hybridization screening can be determined by those skilled in the art.

A specific example of a substantially pure tumor suppressor nucleic acid molecule containing at least fifteen contiguous nucleotides of SEQ ID NO:2 and flanking coding sequence is the tumor suppressor nucleic acid molecule having the nucleotide sequence set forth as SEQ ID NO:5. The isolation of SEQ ID NO:5, based on knowledge of the sequence of SEQ ID NO:2, is described in Example III, below. Similar procedures can be used to identify and substantially purify longer nucleic acid molecules that contain at least fifteen contiguous nucleotides of SEQ ID NO:4. Such molecules and their functional fragments can be used to produce tumor suppressor polypeptides and specific antibodies, by methods known in the art and described herein, for use in the diagnostic and therapeutic methods described below.

As described previously, a tumor suppressor nucleic acid molecule, when functionally inactivated in a cell, causes the cell to proliferate in an unregulated manner. The tumor suppressor activity of a nucleic acid molecule containing at least fifteen contiguous nucleotides of SEQ ID NO:2 or SEQ ID NO:4 and additional native nucleic acid sequences can be further demonstrated using various methods known in the art and described herein. For example, nucleic acid sequences flanking the SEQ ID NO:2 or SEQ ID NO:4 sequences can be selectively targeted in a cell with ribozymes by the methods described in Example V, below. The effect on cell proliferation can be determined by the assays described below. If inactivation by ribozymal cleavage of a second sequence within the isolated nucleic acid molecule also results in unregulated cell proliferation, that nucleic acid molecule is a confirmed tumor suppressor nucleic acid molecule.

Similarly, other types of methods can be used to identify the tumor suppressor activity of a nucleic acid molecule containing at least fifteen contiguous nucleotides of SEQ ID NO:2 or SEQ ID NO:4. For example, an antibody or other selective agent that binds a polypeptide encoded by the nucleic acid molecule can be introduced into the cell, and the effect of the antibody on cell proliferation determined. Similarly, an antisense oligonucleotide that inhibits transcription or translation of the nucleic acid molecule can be introduced into the cell, and the effect of the oligonucleotide on cell proliferation determined. Likewise, the candidate tumor suppressor nucleic acid molecule can be expressed in a cell. An introduced tumor suppressor nucleic acid molecule or its encoded polypeptide will have tumor suppressor activity, and thus inhibit cell proliferation or unregulated cell proliferatiaon. Those skilled in the art can determine other appropriate assays to demonstrate that a substantially pure nucleic acid molecule containing at least fifteen contiguous nucleotides of SEQ ID NO:2 or SEQ ID NO:4 has tumor suppressor activity.

The invention also provides a substantially pure nucleic acid molecule containing substantially the same nucleotide sequence as SEQ ID NO:5, or a functional fragment thereof. The invention further provides a substantially pure nucleic acid molecule encoding substantially the same amino acid sequence as SEQ ID NO:6, or encoding a functional fragment thereof.

SEQ ID NO:5 is a tumor suppressor nucleic acid molecule designated Human Tumor Suppressor-1, or HTS1. The nucleotide sequence of HTS1 is shown in FIG. 6A, and its encoded amino acid sequence (SEQ ID NO:6) is shown in FIG. 6B. Reducing HTS1 mRNA expression in HF cells, using a variety of ribozymes that target HTS1, promotes soft agar colony formation (see Examples II, IV and V, below). Introduction of HTS1 into Hela cells prevents cell proliferation (see Example VI, below).

Thus, a substantially pure nucleic acid molecule containing substantially the same nucleotide sequence as SEQ ID NO:5, or a functional fragment thereof, and a substantially pure nucleic acid molecule encoding substantially the same amino acid sequence as SEQ ID NO:6, or encoding a functional fragment thereof, are tumor suppressor nucleic acid molecules that can be used in the diagnostic and therapeutic methods disclosed herein.

The HTS1 nucleotide sequence (SEQ ID NO:5) disclosed herein has from 96% to 100% identity over portions of its sequence ranging from 98 nucleotides to 447 nucleotides, as determined by BLAST analysis, with human sequences present in the GenBank database having the following Accession numbers: AI084732; AA909530; AI061239; AI147481; AI000807; AA600054; AA281492; AA969975; N34073; AA321112; AI278754; AA989727; AA989727; AA321111; AI285506; AI285506; T16079; AI468710; AA258103; AA310412; AA300789; N40373; AA642297; AA622203; and AA622784. HTS1 (SEQ ID NO:5) also has from 83% to 88% identity over portions of its sequence ranging from 52 nucleotides to 508 nucleotides, as determined by BLAST analysis, with murine sequences present in the GenBank database having the following Accession numbers: AA561626; AA265569; AA237717; AA756790; AA270523; AA517621; W14218; AI325663; AA028364; AA451276; AA068339; W70806; AA475332; AA575760; AA238210; AA239726; AA638785; AA867627; and AI117891. HTS1 (SEQ ID NO:5) also has from 93% identity over a 32 nucleotide portion of its sequence with Dictyostelium discoideum sequences having GenBank Accession numbers AU036921 and C91439, and further has 100% identity over a 21 nucleotide portion of its sequence with Oryctolagus cuniculus sequences having GenBank Accession numbers C82711 and C83567.

A substantially pure nucleic acid molecule containing substantially the same nucleic acid sequence as SEQ ID NO:5, or a functional fragment thereof, does not consist of a nucleotide sequence having the exact endpoints of nucleotide sequences deposited in public databases at the time of filing, such as Expressed Sequence Tags (ESTs), Sequence Tagged Sites (STSs) and genomic fragments, deposited in databases such as the nr, dbest, dbsts, gss and htgs databases, including sequences having the Accession numbers recited above.

A substantially pure nucleic acid molecule containing substantially the same nucleotide sequence as SEQ ID NO:5, or a functional fragment thereof, will be of sufficient length and identity to SEQ ID NO:5 to selectively hybridize to it under moderately stringent hybridization conditions. For example, it can be determined that a substantially pure nucleic acid molecule contains substantially the same nucleotide sequence as SEQ ID NO:5, or is a functional fragment thereof, by determining its ability to hybridize in a filter hybridization assay to a molecule having the sequence of SEQ ID NO:5, but not to other unrelated nucleic acid molecules, under moderately stringent hybridization conditions equivalent to hybridization in 50% formamide, 5× Denhart's solution, 5×SSPE, 0.2% SDS at 42° C., followed by washing in 0.2×SSPE, 0.2% SDS, at 65° C. Suitable alternative buffers and hybridization conditions that provide for moderately stringent hybridization conditions in particular assay formats can be determined by those skilled in the art (see, for example, Sambrook et al., *Molecular Cloning, A Laboratory Manual*, Cold Spring Harbor Laboratory Press, 1989).

The invention further provides a substantially pure hairpin ribozyme nucleic acid molecule, containing a nucleotide sequence selected from the group consisting of SEQ ID NO:1 and SEQ ID NO:3. The hairpin ribozymes of the invention selectively bind, through the substrate binding sequences SEQ ID NO:1 and SEQ ID NO:3, to tumor suppressor mRNA molecules having the ribozyme binding sequences SEQ ID NO:2 and SEQ ID NO:4, respectively. For example, a hairpin ribozyme having the substrate binding sequence of SEQ ID NO:1 binds the HTS1 nucleotide sequence designated SEQ ID NO:18.

A substantially pure hairpin ribozyme of the invention can be catalytic, so as to bind and cleave a tumor suppressor nucleic acid messenger RNA. A catalytic hairpin ribozyme of the invention can therefore be used to selectively regulate the activity of a tumor suppressor nucleic acid molecule of the invention. A substantially pure hairpin ribozyme of the invention can also be catalytically disabled, for example, by replacement of the Loop 2 AAA sequence indicated in FIG. 1 with a UGC sequence, so as to bind, but not cleave, a tumor suppressor nucleic acid molecule of the invention. A non-catalytic hairpin ribozyme can be used, for example, as a control reagent, or as a hybridization probe to identify tumor suppressor nucleic acid molecules in the diagnostic methods described herein.

The nucleic acid molecules of the invention, including tumor suppressor nucleic acid molecules and fragments, and hairpin ribozyme nucleic acid molecules, can be produced or isolated by methods known in the art. The method chosen will depend, for example, on the type of nucleic acid molecule one intends to isolate. Those skilled in the art, based on knowledge of the nucleotide sequences disclosed herein, can readily isolate tumor suppressor nucleic acid molecules as genomic DNA, or desired introns, exons or regulatory sequences therefrom; as full-length cDNA or desired fragments therefrom; or as full-length mRNA or desired fragments therefrom, by methods known in the art. Likewise, those skilled in the art can produce or isolate hairpin ribozymes selective for these sequences.

A useful method of isolating a tumor suppressor nucleic acid molecule of the invention involves amplification of the nucleic acid molecule using the polymerase chain reaction (PCR), and purification of the resulting product by gel electrophoresis. For example, either PCR or reverse-transcription PCR (RT-PCR) can be used to produce a tumor suppressor nucleic acid molecule having any desired nucleotide boundaries. Desired modifications to the nucleic acid sequence can also be introduced by choosing an appropriate primer with one or more additions, deletions or substitutions. Such nucleic acid molecules can be amplified exponentially starting from as little as a single gene or mRNA copy, from any cell, tissue or species of interest.

A further method of producing or isolating a tumor suppressor nucleic acid molecule of the invention is by screening a library, such as a genomic library, cDNA library or expression library, with a detectable agent. Such libraries are commercially available or can be produced from any desired tissue, cell, or species of interest using methods known in the art. For example, a cDNA or genomic library can be screened by hybridization with a detectably labeled nucleic acid molecule having a nucleotide sequence disclosed herein. Additionally, an expression library can be screened with an antibody raised against a polypeptide corresponding to the coding sequence of a tumor suppressor nucleic acid disclosed herein. The library clones containing tumor suppressor nucleic acid molecules of the invention can be purified away from other clones by methods known in the art.

Furthermore, nucleic acid molecules of the invention can be produced by sythetic means. For example, a single strand of a nucleic acid molecule can be chemically synthesized in one piece, or in several pieces, by automated synthesis methods known in the art. The complementary strand can likewise be synthesized in one or more pieces, and a double-stranded molecule made by annealing the complementary strands. Direct synthesis is particularly advantageous for producing relatively short molecules, such as hairpin ribozyme nucleic acid molecules, as well as hybridization probes and primers.

If it is desired to subclone, amplify or express a substantially pure nucleic acid molecule of the invention, the isolated nucleic acid molecule can be inserted into a commercially available cloning or expression vector using methods known in the art. Appropriate regulatory elements can be chosen, if desired, to provide for constitutive, inducible or cell type-specific expression in a host cell of choice, such as a bacterial, yeast, amphibian, insect or mammalian cell. Those skilled in the art can determine an appropriate host and vector system for cloning a nucleic acid molecule of the invention or for expressing and purifying its encoded polypeptide.

Methods for introducing a cloning or expression vector into a host cell are well known in the art and include, for example, various methods of transfection such as the calcium phosphate, DEAE-dextran and lipofection methods, viral transduction, electroporation and microinjection. Host cells expressing tumor suppressor nucleic acid molecules can be used, for example, as a source to isolate recombinantly expressed tumor suppressor polypeptides, to identify and isolate molecules that regulate or interact with tumor suppressor nucleic acids and polypeptides, or to screen for compounds that enhance or inhibit the activity of a tumor suppressor molecule of the invention, as described further below.

The methods of isolating, cloning and expressing nucleic acid molecules of the invention described herein are routine in the art and are described in detail, for example, in Sambrook et al., *Molecular Cloning: A Laboratory Manual*, Cold Spring Harbor Laboratory, New York (1992) and in Ansubel et al., *Current Protocols in Molecular Biology*, John Wiley and Sons, Baltimore, Md. (1989), which are incorporated herein by reference.

The invention also provides a substantially pure polypeptide, containing substantially the same amino acid sequence as SEQ ID NO:6, or a functional fragment thereof. SEQ ID NO:6 is a full-length tumor suppressor polypeptide molecule designated Human Tumor Suppressor-1, or HTS1, which is encoded by SEQ ID NO:5.

The HTS1 amino acid sequence disclosed herein (SEQ ID NO:6) has 36% identity over a 402 amino acid portion, as determined by BLAST analysis, with a *Drosophila melanogaster* polypeptide designated Peter Pan, having GenBank Accession number AAD16459 (AF102805); 36% identity over 340 amino acids with a Caenorhabditis elegans polypeptide having GenBank Accession number 2804465 (AF043700); 37% identity over 289 amino acids with a Schizosaccharomyces pombe polypeptide having GenBank Accession number CAB11063 (Z98531); and 35% identity over 345 amino acids with Saccharomyces cervisiae polypeptides having GenBank Accession numbers Q12153 and P38789.

A substantially pure polypeptide containing substantially the same amino acid sequence as SEQ ID NO:6, or a functional fragment thereof, does not consist of an amino acid sequence having the exact endpoints of amino acid sequences deposited in public databases at the time of filing the application, such as GenBank, EMBL, SwissProt and similar databases, including sequences having the Accession numbers recited above.

Figure 4A:
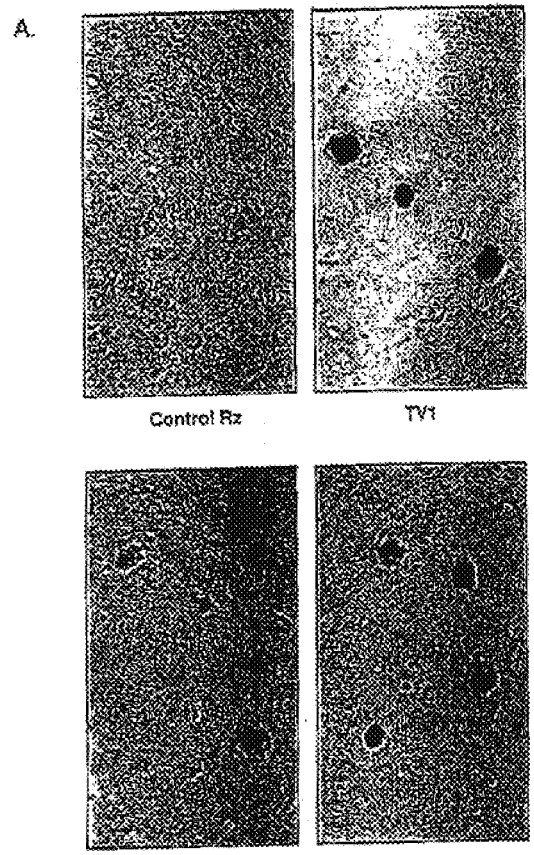
FIG. 4A shows soft agar colonies formed after two rounds of selection in HF cells stably transfected with the indicated target validation (TV) ribozyme expression constructs or a control Rz against HIV.

Furthermore, a substantially pure polypeptide containing substantially the same amino acid sequence as SEQ ID NO:6, or a functional fragment thereof, does not consist of the 137 amino acid *Homo sapiens* polypeptide sequence depicted in FIG. 4 of Migeon et al., *Mol. Biol. Cell.* 10:1733–1744 (1999) (see FIG. 7, "HS," also SEQ ID NO:20), deduced from compilation of expressed sequence tag fragments N34073, N40373, AI147481, AI084732, AA321112, AA300789 and AA258103. Additionally, a substantially pure polypeptide containing substantially the same amino acid sequence as SEQ ID NO:6, or a functional fragment thereof, does not consist of the 358 amino acid *Mus musculus* polypeptide sequence depicted in FIG. 4 of Migeon et al., *supra* (1999) (see FIG. 7, "MM," also SEQ ID NO:19), deduced from compilation of expressed sequence tag fragments AA451276, AA475332, AA068339, AA237717, AA517621, AA270523, AA756790, AA028364, AA575760, AA239726, AA561626, and AA265569.

The isolated tumor suppressor polypeptides and functional fragments of the invention can be prepared by methods known in the art, including biochemical, recombinant and synthetic methods. For example, a tumor suppressor polypeptide can be purified by routine biochemical methods from a cell or tissue source that expresses abundant amounts of the corresponding transcript or polypeptide. The diagnostic methods disclosed herein can be adapted for determining which cells and tissues, and which subcellular fractions therefrom, are appropriate starting materials. Biochemical purification can include, for example, steps such as solubilization of the appropriate tissue or cells, isolation of desired subcellular fractions, size or affinity chromatography, electrophoresis, and immunoaffinity procedures. The methods and conditions for biochemical purification of a polypeptide of the invention can be chosen by those skilled in the art, and purification monitored, for example, by an ELISA assay or a functional assay.

A fragment having any desired boundaries and modifications to the tumor suppressor amino acid sequences disclosed herein can also be produced by recombinant methods. Recombinant methods involve expressing a nucleic acid molecule encoding the desired polypeptide or fragment in a host cell or cell extract, and isolating the recombinant polypeptide or fragment, such as by routine biochemical purification methods described above. To facilitate identification and purification of the recombinant polypeptide, it is often desirable to insert or add, in-frame with the coding sequence, nucleic acid sequences that encode epitope tags, polyhistidine tags, glutathione-S-transferase (GST) domains, and similar affinity binding sequences, or sequences that direct expression of the polypeptide in the periplasm or direct secretion. Methods for producing and expressing recombinant polypeptides in vitro and in prokaryotic and eukaryotic host cells are well known in the art.

Functional fragments of a tumor suppressor polypeptide can also be produced, for example, by enzymatic or chemical cleavage of the full-length polypeptide. Methods for enzymatic and chemical cleavage and for purification of the resultant peptide fragments are well known in the art (see, for example, Deutscher, *Methods in Enzymology*, Vol. 182, "Guide to Protein Purification," San Diego: Academic Press., Inc. (1990), which is incorporated herein by reference).

Furthermore, functional fragments of a tumor suppressor polypeptide can be produced by chemical synthesis. If desired, such as to optimize their functional activity, stability or bioavailability, such molecules can be modified to include D-stereoisomers, non-naturally occurring amino acids, and amino acid analogs and mimetics. Examples of modified amino acids and their uses are presented in Sawyer, *Peptide Based Drug Design*, ACS, Washington (1995) and Gross and Meienhofer, *The Peptides: Analysis, Synthesis, Biology*, Academic Press, Inc., New York (1983), both of which are incorporated herein by reference.

As described previously, a substantially pure polypeptide containing substantially the same amino acid sequence as SEQ ID NO:6, or a functional fragment thereof, has one or more of the functional activities of HTS1 (SEQ ID NO:6). A functional activity can be, for example, immunogenicity, which is an ability to generate an antibody specific for HTS1, or antigenicity, which is an ability to selectively compete with HTS1 for binding to an HTS-1-specific antibody.

Those skilled in the art can determine, by known methods, whether a particular polypeptide or fragment has the immunogenic or antigenic activity of HTS1. For example, to determine whether a polypeptide or fragment has immunogenic activity, the test polypeptide or fragment can be assayed to determine whether it induces a delayed-type hypersensitivity response in an animal sensitized to HTS1. Immunogenic activity can also be determined by elicitation of HTS-1-specific antibodies, as measured by an ELISA assay with HTS1. To determine whether a particular polypeptide or fragment has the antigenic activity of HTS1 and, thus, competes with HTS1 for binding to HTS-1-specific antibodies, various ELISA-type assays, including competitive ELISA, can be performed. Assays that can be used for determining HTS-1-specific immunogenic or antigenic activity of the polypeptides and fragments of the invention are described in more detail in Harlow and Lane, *Antibodies; A Laboratory Manual*, Cold Spring Harbor Laboratory, New York (1989), which is incorporated herein by reference.

If desired, random fragments spanning an entire HTS1 polypeptide sequence can be tested in the assays described above. Alternatively, only those fragments of HTS1 that are likely to be immunogenic or antigenic can be tested. Determination of whether a particular fragment is likely to be immunogenic or antigenic can be based on methods and algorithms known in the art and described, for example, by Margaht et al., *J. Immunol.* 138:2213–2229 (1987) and by Rothbard et al., *EMBO J.* 7:93–100 (1988), which are incorporated herein by reference.

A functional activity of an HTS1 polypeptide or fragment of the invention can also be its ability to alter, such as inhibit or promote, cell proliferation when expressed or introduced in a cell. To determine whether a given polypeptide or fragment has the ability to alter cell proliferation, the polypeptide or fragment can be microinjected into a cell, and an increase or decrease in cell proliferation determined by any of the proliferative assays described below. Alternatively, a polypeptide or fragment can be expressed in the cell by recombinant methods known in the art and as described previously.

Those skilled in the art appreciate that an HTS1 polypeptide that is substantially the same as a full-length native HTS1 tumor suppressor molecule, or that includes an entire tumor suppressing domain therefrom, will likely inhibit cell proliferation upon expression or introduction into a cell. However, a fragment or modification of a tumor suppressor polypeptide that possesses less than an entire tumor suppressing domain, or in which the tumor suppressing activity is inactivated, can compete with the endogenous or recombinantly expressed protein for substrates or regulatory factors., In this case, the modified polypeptide or functional fragment will inhibit the tumor suppressor activity of the endogenous or recombinantly expressed tumor suppressor polypeptide, thereby promoting cell proliferation.

Appropriate assays to determine whether a molecule of the invention alters cell proliferation are known in the art. The skilled artisan appreciates that molecular pathways involved in cell proliferation are generally well conserved among eukaryotic organisms. Therefore, a proliferative assay can be performed in any eukaryotic cell type in which altered proliferation can be detected including, for example, primary mammalian cells, normal and transformed mammalian cell lines, yeast, insect cells and amphibian cells.

A molecule that alters cell proliferation can, for example, cause cell cycle arrest at a particular stage of mitosis or meiosis, induce or prevent apoptosis, or promote progression through the cell cycle when normal cells would arrest. Such qualitative changes in the cell cycle can be determined by methods known in the art, and which depend on the cell type used in the assay. A molecule that alters cell proliferation can also, for example, cause faster or slower progression through the cell cycle, resulting in an increased or decreased number of cells in the population after a given period of time. Those skilled in the art can choose an appropriate assay to determine whether and how a molecule of the invention affects cell proliferation.

A molecule that alters cell proliferation can also restore more normal proliferative characteristics on an abnormally proliferating cell. Such a molecule can advantageously be used in therapeutic applications to treat proliferative disorders. To determine whether a molecule of the invention restores more normal proliferative characteristics on a cell, an assay can be performed in a mammalian cell that exhibits neoplastic proliferative characteristics, such as soft agar colony formation, overgrowth of a cell monolayer, proliferation in low serum, abnormally rapid proliferation, or tumor formation in an animal. Such cells are known in the art and include both tumor cell lines and primary tumor cells. A molecule of the invention can be introduced or expressed in such a cell, and a determination can be made whether the molecule restores more normal proliferative characteristics to the cell, such as slower growth in culture, fewer foci, fewer soft agar colonies, or a reduction in tumor size, as compared to the parental cell.

An HTS1 tumor suppressor molecule that restores normal proliferative characteristics to a neoplastic cell in an assay described above can be administered to an individual, such as a human or other mammal, so as to be introduced or expressed in the neoplastic cell in an amount effective to prevent or inhibit its unregulated proliferation. For example, a nucleic acid molecule encoding a polypeptide that inhibits cell proliferation can be inserted into a mammalian expression vector, such as a plasmid or viral vector, that contains all the necessary expression elements for the constitutive or inducible transcription and translation of the polypeptide, and administered to an individual having, or at risk of developing a tumor.

Useful mammalian expression vectors for gene therapy, and methods of introducing such vectors into cells, are well known in the art. For example, a plasmid expression vector can be introduced into a cell by calcium-phosphate mediated transfection, DEAE-Dextran-mediated transfection, lipofection, polybrene-mediated transfection, electroporation or any other method known in the art of introducing DNA into a cell. A viral expression vector can be introduced into a cell in an expressible form by infection or transduction, for example, or by encapsulation in a liposome. An appropriate viral vector for gene therapy applications can be, for example, a retrovirus, an adenovirus, an adeno-associated virus or a herpes virus.

A physiological composition, such as an aqueous solution, suspension or emulsion, containing an effective concentration of an expressible nucleic acid can be administered by any effective route, such as topically, intraocularly, intradermally, parenterally, orally, intranasally, intravenously, intramuscularly, intraspinally, intracerebrally and subcutaneously. For example, the physiological composition can be directly injected into a solid tumor, tumor-containing organ or tumor containing body cavity, in a effective amount to inhibit proliferation of the tumor cells. Alternatively, the physiological composition can be administered systemically into the blood or lymphatic circulation to reach tumor cells in the circulatory system or in any organ or tissue. Therefore, the tumor suppressor molecules of the invention can be used to treat both solid tumors (carcinomas and sarcomas) and leukemias.

An effective dose of a therapeutic molecule of the invention can be determined, for example, by extrapolation from the concentration required to modulate tumor suppressor nucleic acid or polypeptide expression in the expression assays described herein, or from the dose required to modulate cell proliferation in the proliferation assays described herein.

An effective dose of a molecule of the invention for the treatment of proliferative disorders can also be determined from appropriate animal models, such as xenografts of human tumors in rats or mice. Human cancer cells can be introduced into an animal by a number of routes, including subcutaneously, intraveneously and intraperitoneally. Following establishment of a tumor, the animals can be treated with different doses of a molecule of the invention, and tumor mass or volume can be determined. An effective dose for treating cancer is a dose that results in either partial or complete regression of the tumor, reduction in metastasis, reduced discomfort, or prolonged lifespan.

The appropriate dose for treatment of a human subject with a therapeutic molecule of the invention can be determined by those skilled in the art, and is dependent on the nature and bioactivity of the particular compound, the desired route of administration, the gender, age and health of the individual, the number of doses and duration of treatment, and the particular condition being treated.

The invention also provides an antibody or antigen binding fragment thereof specifically reactive with an HTS1 tumor suppressor polypeptide or functional fragment of the invention. Such antibodies can be used, for example, to affinity purify an HTS1 polypeptide from a cell or tissue source. Such antibodies can also be used to detect the expression of the polypeptide in a sample, or to selectively detect an abnormal structural variant of the polypeptide, in the diagnostic methods described herein. An antibody can be labeled with a detectable moiety so as to render it detectable by analytical methods. For example, a detectable moiety can be directly or indirectly attached to the antibody. Useful detectable moieties include, for example, enzymes, fluorogens, chromogens, chemiluminescent labels and secondary binding agents.

Antibodies that selectively detect an abnormal structural variant of HTS1 can also be administered therapeutically, to selectively target cells that express the altered copy of the polypeptide. If desired, such antibodies can be administered in conjuction with a cytotoxic or cytostatic moiety, such as a radioisotope or toxin, in order to neutralize or kill cells expressing the abnormal structural variant.

An antigen binding fragment of an antibody of the invention includes, for example, individual heavy or light chains and fragments thereof, such as VL, VH and Fd; monovalent fragments, such as Fv, Fab, and Fab'; bivalent fragments such as $F(ab')_2$; single chain Fv (scFv); and Fc fragments. Antigen binding fragments include, for example, fragments produced by protease digestion or reduction of an antibody, as well as fragments produced by recombinant DNA methods known to those skilled in the art.

The antibodies of the invention can be produced by any method known in the art, and can be polyclonal or monoclonal. For example, a polypeptide or immunogenic fragment of the invention, or a nucleic acid expressing such a polypeptide, can be administered to an animal, using standard methods, and the antibodies isolated therefrom. The antibodies can be used in the form of serum isolated from an immunized animal or the antibody can be purified from the serum. Additionally, the antibodies can be produced by a hybridoma cell line, by chemical synthesis, or by recombinant methods. Modified antibodies, such as chimeric antibodies, humanized antibodies and CDR-grafted or bifunctional antibodies, can also be produced by methods well known to those skilled in the art.

Methods of preparing and using antibodies and antigen-binding fragments, including detectably labeled antibodies, are described, for example, in Harlow and Lane, *Antibodies: A Laboratory Manual*, Cold Spring Harbor Laboratory, New York (1989); in Day, E. D., *Advanced Immunochemistry*, Second Ed., Wiley-Liss, Inc., New York, N.Y. (1990); and in Borrebaeck (Ed.), *Antibody Engineering*, Second Ed., Oxford University Press, New York (1995), which are incorporated herein by reference.

As described herein, functional inactivation of a tumor suppressor molecule of the invention by cleavage of the mRNA with a hairpin ribozymes promotes unregulated, neoplastic proliferation. Therefore, by detecting functional inactivation of a tumor suppressor molecule in a sample, one can detect the presence of a neoplastic cell in the sample. In an individual with a neoplasia, inactivation of the tumor suppressor nucleic acid molecule could have occurred by any of a variety of different mutational mechanisms including, for example, frameshift mutations, nonsense mutations, deletions and rearrangements, which alter the expression or structure, and thus affect the normal function, of the tumor suppressor molecule. In different neoplastic cell types, and at different stages in tumor development, it is expected that different mutational events will have occurred.

The invention thus provides a method of detecting a neoplastic cell in a sample. In one embodiment, the method consists of contacting the sample with a detectable agent specific for a tumor suppressor nucleic acid molecule of the invention, and detecting the nucleic acid molecule in the sample. Altered expression or structure of the nucleic acid molecule indicates the presence of a neoplastic cell in the sample. In another embodiment, the method consists of contacting the sample with a detectable agent specific for a tumor suppressor polypeptide of the invention, and detecting the polypeptide in the sample. Altered expression or structure of the polypeptide indicates the presence of a neoplastic cell in the sample.

The diagnostic methods described herein are applicable to the identification of neoplastic cells present in solid tumors (carcinomas and sarcomas) such as, for example, breast, colorectal, gynecological, lung, prostate, bladder, renal, liver, urethral, endocrinal, melanoma, basal cell central nervous system, lymphoma, stomach, esophageal, squamous cell cancers, as well as all forms of leukemia and lymphoma.

Various qualitative and quantitative assays to detect altered expression or structure of a nucleic acid molecule in a sample are well known in the art, and generally involve hybridization of a detectable agent, such as a complementary primer or probe, to the nucleic acid molecule. Such assays include, for example, in situ hybridization, which can be used to detect altered chromosomal location of the nucleic acid molecule, altered gene copy number, or altered RNA abundance, depending on the format used. Other assays include, for example, Northern blots and RNase protection assays, which can be used to determine the abundance and integrity of RNA; Southern blots, which can be used to determine the copy number and integrity of DNA; SSCP analysis, which can detect single point mutations in DNA, such as in a PCR or RT-PCR product; and coupled PCR, transcription and translation assays, such as the Protein Truncation Test, in which a mutation in DNA is determined by an altered protein product on an electrophoresis gel. An appropriate assay format and detectable agent to detect an alteration in the expression or structure of a tumor suppressor nucleic acid molecule can be determined by one skilled in the art depending on the alteration one wishes to identify.

Various assays to detect altered expression or structure of a polypeptide of the invention are also well known in the art, and generally involve hybridization of a detectable agent, such as an antibody or selective binding agent, to the polypeptide in a sample. Such assays can be performed in situ, such as by immunohistochemistry or immunofluorescence, in which a detectably labeled antibody contacts a polypeptide in a cell. Other assays, for example, ELISA assays, immunoprecipitation, and immunoblot analysis, can be performed with cell or tissue extracts. Assays in which the polypeptide remains in a native form are particularly useful if a conformation-specific binding agent is used, which can detect a polypeptide with an altered structure. A structural variant of a tumor suppressor polypeptide can act, for example, in a dominant-negative fashion to inactivate a normal regulatory pathway and cause unregulated cell proliferation. An appropriate assay format and detectable agent to detect an alteration in the expression or structure of a tumor suppressor polypeptide can be determined by one skilled in the art depending on the alteration one wishes to identify.

The diagnostic methods described herein can also be adapted for use as prognostic assays. Such an application takes advantage of the observation that alterations in expression or structure of different tumor suppressor molecules take place at characteristic stages in the progression of a proliferative disease or of a tumor. Knowledge of the stage of the tumor allows the clinician to select the most appropriate treatment for the tumor and to predict the likelihood of success of that treatment. The diagnostic methods described herein can also be used to monitor the effectiveness of therapy. Successful therapy can be indicated, for example, by a reduction in the number of neoplastic cells in an individual, as evidenced by more normal expression and structure of the tumor suppressor molecules of the invention in a sample following treatment.

In the diagnostic and prognostic assays described herein, the abundance or structure of the detected nucleic acid or polypeptide in the test sample is compared to the known abundance or structure of the nucleic acid or polypeptide in a normal sample. The normal sample can be obtained either from normal tissue of the same histological origin of the same or a different individual.

The invention further provides a method of identifying cellular and non-cellular molecules that selectively bind, mimic or regulate the tumor suppressor molecules of the invention. Various binding assays to identify cellular proteins that interact with protein binding domains are known in the art and include, for example, yeast two-hybrid screening assays (see, for example, Luban et al., *Curr. Opin. Biotechnol.* 6:59–64 (1995)) and affinity column chromatography methods using cellular extracts. Additionally, binding compounds can be identified by screening libraries of compounds, including chemical or biological molecules such as simple or complex organic molecules, metal-containing compounds, carbohydrates, peptides, proteins, peptidomimetics, glycoproteins, lipoproteins, nucleic acids, antibodies, and the like, using methods known in the art.

Compounds that selectively bind to tumor suppressor molecules can be used, for example, to detect the presence, abundance or structural integrity of tumor suppressor molecules in the diagnostic methods described herein. Compounds that mimic or activate the tumor suppressor molecules of the invention in cell-based assays can be used, for example, as therapeutics to treat proliferative disorders such as cancer, either alone or when attached to a cytotoxic or cytostatic agent. The proliferative assays described herein can be used to identify compounds that mimic or activate tumor suppressor biological activity and are thus appropriate therapeutic compounds to treat cancer.

It is understood that modifications which do not substantially affect the activity of the various embodiments of this invention are also included within the definition of the invention provided herein. Accordingly, the following examples are intended to illustrate but not limit the present invention.

EXAMPLE I

Preparation of the Random Retroviral Vector Ribozyme Library

This example demonstrates the construction of a random retroviral plasmid ribozyme gene library. The inventors have discovered that by introducing a random retroviral plasmid ribozyme gene library into the Hela cell revertant cell line, HF, certain of the ribozymes will selectively target and inactivate mRNA molecules encoding tumor suppressor genes. If the ribozyme has inactivated a tumor suppressor nucleic acid molecule, the HF cells will proliferate in an unregulated fashion and form soft agar colonies. The ribozyme genes are then rescued from these soft agar colonies and sequenced across their substrate binding sites. The corresponding ribozyme binding sequence, or "ribozyme sequence tag" (RST) is a sequence present in the tumor suppressor nucleic acid molecule targeted by the ribozyme. Thus, knowledge of the RST allows novel tumor suppressor nucleic acids to be identified and isolated.

A plasmid-based retroviral library was constructed by inserting random ribozyme gene sequences into parent vector pLHPM-2kb. pLHPM-2kb contains 5' and 3' long terminal repeats (LTR) of the Moloney retroviral genome; a neomycin resistance gene driven by the LTR; an SV40 promoter driving a puromycin resistance gene; and a transcription cassette containing a tRNAval promoter and a 2 kb stuffer insert. When the stuffer insert is removed and replaced by the random ribozyme library inserts, the tRNAval promoter can drive transcription of the inserted ribozyme gene.

To prepare the pLHPM-2kb vector, plasmid pLHPM was digested overnight at 65° C. with BstB1, phenol:chloroform extracted and ethanol precipitated. The resuspended DNA was then digested overnight at 37° C. with MluI. This double digestion excises the 2kb stuffer fragment. The resultant 6kb plasmid vector DNA fragment was purified by agarose gel electrophoresis.

To prepare the random ribozyme library inserts, three oligonucleotides were synthesized and annealed in annealing buffer (50 mM NaCl, 10 mM Tris pH 7.5, 5 mM MgCl2) at a molar ratio of 1:3:3 (oligo1:oligo2:oligo3) by heating to 90° C. followed by slow cooling to room temperature. The three oligonucleotides had the following sequences:

Oligo1: 5'-pCGCGTACCAGGTAATATACCACGGA CCGAAGTCCGTGTGTTTCT CTGGTNNNNTTCTN NNNNNNNGGATCCTGTTTCCGCCCGGTTT-3' (SEQ ID NO:7)

Oligo2: 5'-pGTCCGTGGTATATTACCTGGTA-3' (SEQ ID NO:8)

Oligo3: 5'-pCGAAACCGGGCGGAAACAGG-3' (SEQ ID NO:9)

To provide for random and uniform incorporation of A, T, C and G nucleotides at the positions represented as N nucleotides in oligo1, the A, T, C and G reagents were premixed, and the same mixture used for every N position in the oligonucleotide synthesis. The ribozyme insert library formed by annealing the three oligonucleotides (SEQ ID NOS:7–9) thus contains 8 positions with random nucleotides corresponding to helix 1 of the ribozyme, and 4 random positions with random nucleotides corresponding to helix 2 of the ribozyme.

In order to ligate the pLHPM-2kb vector DNA fragment with the random ribozyme insert library, 0.5 pmole of the vector and an 8-fold molar excess of annealed oligonucleotides were ligated overnight with 10 units of T4 DNA ligase. Ultracompetent DH12S bacteria were then electroporated with the ligation mixture. A total of $5 \times 10^7$ bacterial colonies containing the retroviral plasmid ribozyme library was obtained.

The bacterial colonies containing the retroviral plasmid ribozyme library were pooled in aliquots as a master stock and frozen at −80° C. Working stocks were made by culturing 1 ml of the master stock in 60 ml LB media overnight at 30° C. A 1 ml aliquot of the working stock was used to make a 500 ml bacterial culture by incubation at 30° C. overnight. Plasmid DNA was then extracted from the 500 ml culture and transfected into HF revertant cells, as described in Example II, below.

Following the cloning of the randomized hairpin ribozyme genes into pLHPM, the "randomness" of the plasmid library was evaluated by both statistical and functional analyses. A complete ribozyme library of this design, with 12 random positions, would contain 412, or $1.67 \times 10^7$, different members. For the statistical analysis, forty individual bacterial transformants were picked and sequenced. This allowed an evaluation of the complexity of the library without having to manually sequence each library member. The statistical "randomness" of the library was determined utilizing the formula for a two-sided approximate binomial confidence interval: $E = 1.96 * \text{squareroot}(P*(1-P)/N)$, where P=the expected proportion of each nucleotide in a given position (this value for DNA bases equals 25% or P=0.25), E=the desired confidence interval around P (i.e. P+/−E) and N=the required sample size (Callahan Associates, Inc., La Jolla, Calif.). To determine the proportion of each base within 5% (E=0.05), the required sample size is 289. Since each ribozyme molecule contains twelve independent positions, the number of individual ribozyme genes that need to be sequenced out of the library equals 289 divided by 12, or about 25 molecules.

The frequencies of the four nucleotides, with 95% confidence limits, in the random positions were calculated to be G: 22.3±6.1, A: 3 1.9±7.0, T: 27.3±7.8 and C: 18.01±15.1. Since the expected frequency for each base is 25%, each base appears to be randomly represented (except for C, which may be slightly lower than expected). These variations most likely result from the unbalanced incorporation of nucleotides during the chemical synthesis of the oligonucleotides and could reduce the complexity of the library.

For a functional evaluation of the library's complexity, in vitro cleavage was utilized to determine if ribozymes that target known RNA substrates were present in the library pool. This involved in vitro transcribing of the entire ribozyme library in one reaction and then testing the pool's ability to cleave a variety of different RNA substrates of both cellular and viral origin. Six out of seven known RNA targets were properly and efficiently cleaved by the in vitro transcribed library. This qualitative analysis suggested a significantly complex library of ribozyme genes and the lack of cleavage of one target out of seven may reflect the slight non-randomness suggested by the base composition described above.

EXAMPLE II

Isolation of Ribozymes that Target Tumor Suppressor Nucleic Acids

This example demonstrates the isolation of ribozyme genes that bind to and inactivate tumor suppressor nucleic acid molecules, and the identification of the nucleic acid sequences they target.

The Hela revertant cell line, HF, used in these experiments was produced by exposure of Hela cervical carcinoma cells to the mutagen EMS, and subsequent isolation of a stable clone that had lost transforming properties. The HF cell line is described by Boylan et al., *Cell Growth Differ*. 7:725–735 (1996). In contrast to Hela cells, HF cells do not exhibit a transformed morphology and are non-tumorigenic in nude mice. HF cells are also anchorage dependent, as evidenced by a very low cloning efficiency in soft agar (0.05%), compared with 20% for the parental Hela cells. Boylan et al., *supra* (1996) observed that fusion of HF cells with Hela cells resulted in a loss of the transformed phenotype in the fusion cells. This observation indicated that the HF cells express one or more dominant tumor suppressor genes.

Both Hela and HF cells were cultured at 37° C. in DMEM (Gibco BRL) supplemented with 10% FBS, L-gln, sodium pyruvate and antibiotics. For stable library delivery, $1\times10^8$ HF cells were transfected with the ribozyme plasmid library using the BES-calcium phosphate method. 24 hours post transfection, cells were selected with G418 (500 pg/ml) for two weeks. Approximately $1\times10^7$ stable transfectants were generated following G418 selection as determined by colony formation, and all colonies were pooled prior to soft agar selection.

To determine whether any of the transfectants had regained their transformed phenotype, soft agar selection of the library was performed in forty 150 mm$^2$ plates, pre-layered with 12 ml of a 1:1 mixture of 1.2% Select Agar (GibcoBRL, Rockville, Md.): 2×MEM/20% FBS. After the pre-layer had solidified, $3\times10^5$ cells were plated in the "cell layer" consisting of 12 ml of a 1:1 mixture of 0.6% Select Agar: 2×MEM/20% FBS. As a control, $1.2\times10^6$ HF cells stably transfected with an unrelated Rz, CNR3, were plated into four 150 mm$^2$ soft agar plates. As comparisons, $3\times10^5$ Hela or HF parental (untransfected) were plated into one 150 mm$^2$ plate each. The cell layers were allowed to solidify prior to incubation at 37° C. Soft agar plates were fed once per week by layering 8 ml freshly prepared 1:1 mixture of 0.6% Agar Select: 2×MEM/20% FBS. Colonies were visible by two weeks and picked for expansion and analysis at 3 weeks. Following three weeks in soft agar, colonies appeared in both the Rz library and CNR3 control Rz, however the library-expressing cells produced 2.5-fold more colonies than the control Rz and 4-fold more than untransfected HF cells (Table 1).

TABLE 1

| Cells | Primary Selection (colonies/10$^5$) | Secondary Selection (colonies/10$^5$) |
| --- | --- | --- |
| Hela | 50,000 | 50,000 |
| HF Parental | 10 | 25 |
| HF-Control Rz | 20 | 48 |
| HF-Rz Library | 45 | 15,000 |

To determine whether the cells that grew as colonies in soft agar had a stable phenotype, 300 colonies from the library expressing cells, 100 colonies from the CNR3 HF-control, or 30 colonies from either Hela or HF parental were picked from the first round, pooled and expanded for 2 weeks in normal media. Second round soft agar selection was performed with $3\times10^5$ cells in one 150 mm$^2$ plate for each cell type. Both the HF parental and the HF$^-$ control cells showed only modest (2- to 3-fold) enrichment in soft agar growth, indicating that colony growth in the controls was mostly due to unstable, stochastic processes. In contrast, the library-expressing cells showed a dramatic 300-fold increase, suggesting that ribozymes from the library stably enhanced soft agar growth (Table 1).

Two methods of ribozyme gene rescue were performed in parallel, viral rescue and PCR rescue, on the pool of 300 colonies from the first round of soft agar selection. The first method, viral rescue, takes advantage of the fact that the Rz expression cassette is located between packagable retroviral LTRs. Rz-expressing cells were transiently transfected with the retroviral gag, pol and VSV-G envelope genes using the lipid transfection reagent LT1 (available from Miris Laboratories, distributed by Panvera, Inc.). 6.3 $\mu$g each pEnv- (Moloney gag and pol) and pVSV-G (vesicular stomatitis virus G glycoprotein to serve as the retroviral envelope) per 100 mm$^2$ dish, according to the manufacturer's instructions. 24–48 hours later, viral supernatant was recovered and filtered (0.2 $\mu$m) prior to transduction of fresh HF cells in the presence of 4 $\mu$g/ml polybrene. Fresh HF cells were then transduced with the infectious supernatant, selected with G418 and plated into soft agar. Sequence analysis from the resulting individual soft agar colonies revealed enrichment of one ribozyme, designated Rz 568, present in three out of ten clones.

The second method of Rz gene rescue was performed by PCR amplification of the genomic DNA from the selected pool of cells, followed by batch recloning of the Rz genes into the pLHPM vector. PCR rescue was performed on genomic DNA, isolated from the selected cells using the QIAamp Blood Kit (Qiagen, Valencia, Calif.). PCR primers within the vector amplified a 300 bp fragment containing the ribozyme genes. The PCR product, which contained a pool of Rz genes, was then digested with BamHI and MluI and ligated into pLHPM digested with the same enzymes. The resulting bacterial clones were pooled and purified DNA was used for cell transfections. Fresh HF cells were stably transfected and plated into soft agar. In this rescue, Rz 568 was present in five out of ten soft agar colonies.

Sequence results from the viral and PCR rescues suggested that Rz 568 was conferring a selective growth advantage to HF cells plated in soft agar. To verify this finding, the 568 ribozyme gene was stably transfected into fresh HF cells as described above. As a control, the catalytically disabled form of Rz 568 (d568, see FIG. 1) was similarly cloned and transfected. After two rounds of selection, Rz 568, but not d568, significantly promoted HF soft agar growth (FIG. 2), verifying that Rz 568 alone can confer this phenotype. Equally important, since d568 had no effect, it was concluded that the catalytic activity of Rz 568 is required for the phenotype, presumably by cleaving an mRNA involved in an anchorage-dependent growth pathway active in HF cells.

The substrate binding sequence of Rz 568, together with its corresponding ribozyme sequence tag (RST 568), is presented in Table 2, below.

TABLE 2

| Rz 568 gene sequence | Corresponding RST 568 |
| --- | --- |
| ACCTCCCC AGAA CCCT (SEQ ID NO:1) | AGGG NGTC GGGGAGGT (SEQ ID NO:2) |

A second ribozyme gene was identified by the viral rescue procedure described above. Rz 619 has a stronger phenotype that Rz 568, ie. produces a higher number of soft agar colonies after transfection of HF cells. Expression of Rz 619 alters the morphology of HF cells to a transformed, highly refractile appearance. Rz 619 does not target the HTS1 mRNA, nor does it have any obvious database matches. The substrate binding sequence of this ribozyme (Rz 619), and its corresponding ribozyme sequence-tag, designated RST 619, is presented in Table 3, below.

TABLE 3

| Rz 619 gene sequence | Corresponding RST 619 |
|---|---|
| AGAGTGTA AGAA ACTA (SEQ ID NO:3) | TAGT NGTC TACACTCT (SEQ ID NO:4) |

In view of their ability to reproducibly cause a transformed phenotype when expressed in HF revertant cells, ribozymes containing substrate binding sequences designated SEQ ID NO:1 and SEQ ID NO:3 are ribozymes which target and inactivate tumor suppressor nucleic acid molecules. Likewise, the targets of these ribozymes, which are nucleic acid molecules containing nucleic acid sequences designated SEQ ID NO:2 or SEQ ID NO:4, are tumor suppressor nucleic acid molecules.

EXAMPLE II

Isolation and Characterization of Human Tumor Suppressor-1 (HTS1)

This example demonstrates the isolation of a full-length tumor suppressor nucleic acid molecule designated Human Tumor Suppressor-1 (HTS1) cDNA and its encoded polypeptide.

Since ribozymes recognize their cognate targets by sequence complementarity, the sequence of a ribozyme that causes a phenotype through its catalytic activity predicts a sequence tag that can be used to clone the target gene. This "Ribozyme Sequence Tag" or RST is 16 bases long, consisting of the two target binding arms (helix 1 and 2) and the requisite GUC in the target (FIG. 1A). The RST can thus be used to BLAST search the gene and EST databases, and also can be used as a primer for 3' and 5' RACE. BLASTS of the EST databases yielded several hits, mostly of genes with unknown function. None of the database hits appeared to be related to tumor suppression, cancer or anchorage-dependent growth.

In light of the absence of obvious database hits, the RZ 568 target gene was cloned using the 568 RST as a primer for 5'RACE (Rapid Amplification of cDNA Ends). For 5'RACE, polyA+mRNA was prepared from HF cells using the Poly(A)Pure kit (Ambion, Austin, Tex.). The mRNA was used as template for the Marathon cDNA amplification kit (Clontech, Palo Alto, Calif.). Briefly, a first strand cDNA was synthesized from the mRNA and used as a template in a second strand synthesis reaction. The ends of the double stranded cDNAs were made blunt with Klenow enzyme and adapters were ligated to the blunt ends. 5' RACE was performed with a primer complementary to the adapters (API, 5'CCATCCTAATACGACTCACTATAGGGC3' (SEQ ID NO:11)) and a primer which matches the target recognition site of Rz 568 (5'CGATGCTCCTCTAGACTC-GAGGGTACCACCTCCCCGACNCCCT3' (SEQ ID NO:12); the 568 sequence is underlined). The PCR reaction was performed with primer concentrations of 200 nM, AmpliTaq Gold polymerase (Perkin Elmer, Branchburg, N.J.) and the following cycle parameters: initial incubation at 94° C. for 10 minutes, followed by five 30 second cycles at 94° C., one 4 minute cycle at 68° C.; twenty eight 30 second cycles at 94° C., one 30 second cycle at 59° C., one 4 minute cycle at 68° C., and finally one 7 minute cycle at 72° C. The reactions products were gel purified and cloned into a TA cloning vector (Invitrogen, Carlsbad, Calif.).

Several PCR products were generated from HF mRNA. To verify the presence of a complete 568 target site in these messages, larger gene-specific primers were designed to perform 3'RACE. 3'RACE was performed using HF polyA+ mRNA in a reverse transcription reaction using an anchored polyT-TAG primer (5'GGCCACGCGTCGACTAG-TACTTT TTTTTTTTTTTTV3' (SEQ ID NO:13), where V is either G, A or C) using Superscript reverse transcriptase (GibcoBRL, Rockville, Md.) according to the manufacturer's instructions. PCR was performed using a gene specific primer for HTS1 (5'CGGCTCACCGAGATCGGCCC3' (SEQ ID NO:14)) and a primer for the polyT TAG region (5'GGCCACGCGTCGACTAGTACT3' (SEQ ID NO:15)) using the following cycle parameters: initial incubation for 10 minutes at 94° C. followed by thirty-five 30 second cycles at 94° C., one 30 second cycle at 55° C., and finally one 4 minute cycle at 72° C. The resulting PCR product was gel purified and cloned into a TA cloning vector.

One of the fragments contained the 568 RST as determined by 3'RACE and sequencing. This cDNA had matches to several incomplete cDNAs in the human EST databases. The deduced amino acid sequence had homology to a Drosophila gene, designated peter pan (ppan), that was shown to be involved in cell growth, DNA replication and possibly cell-cell communication during development (Migeon et al., Mol. Biol. Cell. 10:1733–1744 (1999); GenBank accession number AF102805))

To clone the rest of HTS1 cDNA, a 20-bp gene-specific primer was used in a 3'RACE, and the 5' and 3' RACE products were ligated together using the common HgaI site. The final ligation product was verified by overlapping sequencing reactions in both directions. The cDNA contains a Kozak ATG translation start site at nucleotide position 103, which is believed to be the start of the protein reading frame due to the fact that a stop codon is present upstream of, and in frame with, this ATG. The region codes for a 473 amino acid protein with a calculated molecular weight of approximately 53 kD. The nucleotide sequence of HTS1 (SEQ ID NO:5) and its predicted amino acid sequence (SEQ ID NO:6), are shown in FIG. 6. The nucleotide sequence targeted by Rz 568 is between nucleotides 965 and 979 of the sequence shown in FIG. 6A (SEQ ID NO:5), and has the sequence: 5'AGGGCGTCGGGGAGG3' (SEQ ID NO:18).

The HTS1 gene appears to be the homolog of Drosophila ppan, and thus has been designated herein hPPAN. This gene appears to be conserved evolutionarily and includes homologs in mouse, Drosophila, C. elegans, yeast and Arabidopsis. An alignment of hPPAN with homologs from mouse (Mus musculus, compilation of ESTS AI325663, AA756790 and AA575760) and Drosophila melanogaster is shown in FIG. 3B.

Migeon et al., supra (1999) reported hPPAN and murine PPAN amino acid sequences, based on compilation of EST fragments. The sequences reported by Migeon et al. differ from the sequences obtained from direct cloning of the cDNA. This is most likely due in part to the incompleteness of the available ESTs and their proposed compilation.

EXMPLE IV

Expression of Human Tumor Suppressor-1 (HTS1)

This example demonstrates the expression of HTS1 (hPPAN) mRNA in Hela and HF cells, and the effect of Rz 568 on HTS1 expression.

To determine if Rz 568 affected the mRNA levels of hPPAN in HF cells, Northern analysis was performed using the full length hPPAN CDNA. Total cellular RNA was prepared using the RNAgents K (Promega, Madison, Wis.) and 20 μg total RNA was electrophoresed on formaldehyde gels using standard procedures. RNA was transferred to Zeta-Probe membranes (Bio-Rad, Cambridge, Miss.) by capillary action, as recommended by the manufacturer. Northern hybridizations were performed with QuikHyb (Stratagene, La Jolla, Calif.) according to their instructions, using the full length hPPAN cDNA random-prime labeled with the High Prime DNA labeling kit (Boehringer Mannheim, Indianapolis, Ind.). Northern signals were quantitated by phosphorimager (Molecular Dynamics, Sunnyvale, Calif.), and data averaged from three to four independent experiments were plotted. hPPAN mRNA levels were normalized to internal G3PDH mRNA and values reported as a percentage, where HF was set to 100%.

Northern blotting identified a single 1.6 kb band. Cells stably expressing Rz 568 consistently showed a 30–35% reduction in hPPAN expression relative to a G3PDH internal control (FIG. 3B) while neither d568 nor the unrelated Rz CNR3 had any significant effect on hPPAN mRNA levels. A 10–20% difference in hPPAN levels in Hela vs. HF cells was observed consistently, which implies that hPPAN expression may contribute to the phenotypic differences observed between Hela and HF.

EXAMPLE V

Validation of the Role of HTS1 (hPPAN) in Anchorage-dependent Growth

This example shows that knockdown of HTS1 mRNA by several different ribozymes promotes soft agar colony formation in HF cells, confirming that HTS1 is a tumor suppressor gene.

To confirm that the Rz 568-mediated knockdown of HTS1 (hPPAN) mRNA in HF cells was truly promoting soft agar growth, several other ribozymes were designed against other GUC sites within the hPPAN mRNA. Five "target validation" ribozyme sites were chosen within HTS1. TV 1, 2 and 3 were all located within 150 bases of the 568 Rz site where it was considered that the RNA secondary structure would be sufficiently open and available for cleavage. TV4 and 5 were chosen near the 5' end of the mRNA, at or before the ATG translation start site, which has been shown to often be accessible and vulnerable to ribozyme-mediated cleavage in vivo. A ribozyme targeting human immunodeficiency virus was used as a control.

The locations of the target validation ribozyme sites are between nucleotides 3–18 (TV4), 106–121 (TV5), 808–823 (TV1), 866–881 (TV2) and 1163–1178 (TV3) of the nucleotide sequence shown in FIG. 6A (SEQ ID NO:5).

The target validation ribozyme genes (as well as control ribozyme genes) were digested with BamHI and MluI and ligated into pLHPM digested with the same enzymes. Each vector contained a different selectable antibiotic marker. Ribozyme sequences were verified by DNA sequencing prior to cell transfections.

Since some Rz may be more active than others, one or two TV Rz genes were stably transfected into HF cells, followed by soft agar selection as described above in Example II. All TV transfections yielded prominent soft agar growth while transfection of a control Rz had no effect (FIG. 4A), strongly suggesting that HTS1 was indeed the phenotypically relevant target of the 568 Rz. As further confirmation, three Rz were designed against each of two different (not hPPAN) ESTs of unknown function that came out of a 568 BLAST search. None of those six Rz, alone or in combinations of three, showed any soft agar growth above background. These data further implicate HTS1 in the soft agar phenotype.

Figure 4B:
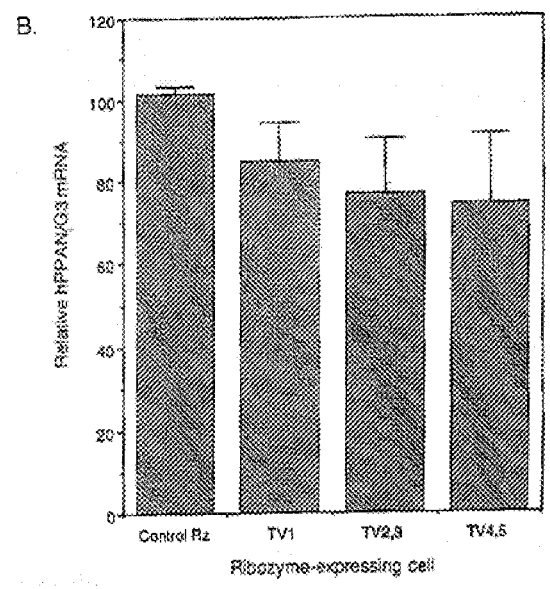
FIG. 4B shows Northern blot analysis of HTS1 (hPPAN) mRNA levels relative to G3PDH mRNA in cells expressing target validation Rz or control Rz.

Additionally, each of the TV-transfected cell populations, but not the control, showed a reduction in hPPAN mRNA following soft agar selection, as shown in FIG. 4B, thus linking the soft agar phenotype with ribozyme-mediated knockdown of hPPAN.

Under soft agar growth conditions, mechanisms active in HF cells sense their lack of substrate contact and prevent their proliferation, apparently undergoing apoptosis. When Rz 568 reduces the level of hPPAN in these cells, soft agar growth resumes. These results imply that HTS1 is part of a pathway that provides a cell with information about its substrate contact and may be involved in the metastatic potential of transformed cells.

EXAMPLE VI

Effect of Overexpression of HTS1

This example shows that overexpression of HTS1 prevents Hela cell growth.

If HTS1 (hPPAN) was indeed involved in preventing HF growth in soft agar, it was hypothesized that overexpression of HTS1 in transformed Hela cells should block their ability to grow in soft agar. To test this hypothesis, the wild type HTS1 and a frameshift mutant of HTS1 were expressed in both Hela and HF cells under the control of the CMV promoter. In this plasmid, the CMV transcript is designed to be bicistronic with the ECMV IRES initiating translation of the hygromycin resistance gene. Therefore, resistance to hygromycin indicates expression of HTS1 cDNA as well.

To create the frameshift (FS) mutant of HTS1, the unique BssHII site at nucleotide position 135 (amino acid 12) was digested and the overhanging ends were filled in with Klenow polymerase. The resulting blunt ends were re-ligated, thus shifting the coding frame by 1 base. The frameshift was verified by DNA sequencing and this new reading frame continues for 53 amino acids before a translation stop.

Expression of HTS1 (hPPAN) or the corresponding frameshift mutation (FS) had no effect on the growth of HF cells compared to the vector alone, as determined by the number of stable hygromycin resistant colonies following transfection and selection (FIG. 5, left panels). However, expression of the wild type hPPAN in Hela cells resulted in a sharp decrease in the number of hygromycin-resistant colonies as compared to its frameshifted control (FIG. 5, right panels). This inability to select stable hPPAN expressing cells preventing testing the hypothesis that hPPAN would block Hela soft agar growth. Indeed, overexpression of hPPAN appears to block all Hela cell growth.

These results suggest that endogenous HTS1 (hPPAN) may not signal when the cell is on an inappropriate substrate, perhaps due to additional regulators downstream. Overexpression of hPPAN may override this control, sending a constitutive signal that the cell is on an inappropriate substrate. hPPAN-induced death in Hela cells may be via an apoptotic pathway or some type of cell cycle arrest.

Throughout this application various publications and database Accession numbers have been referenced. The disclosures of these publications and Accession number nucleotide and amino acid sequences, in their entireties, are hereby incorporated by reference in this application in order to more fully describe the state of the art to which this invention pertains.

What is claimed is:

1. A substantially pure nucleic acid molecule comprising a nucleic acid sequence that has greater than 95% sequence identity with the nucleic acid sequence shown as SEQ ID NO:5, wherein said nucleic acid molecule encodes a polypeptide that functions as a tumor suppressor molecule.

2. A substantially pure tumor suppressor nucleic acid molecule encoding the amino acid sequence shown as SEQ ID NO:6.

3. The substantially pure nucleic acid molecule of claim 1 wherein said nucleic acid molecule comprises the nucleic acid sequence shown as SEQ ID NO:5.

* * * * *

SEQUENCE LISTING

<160> NUMBER OF SEQ ID NOS: 20

<210> SEQ ID NO 1
<211> LENGTH: 16
<212> TYPE: RNA
<213> ORGANISM: Artificial Sequence
<220> FEATURE:
<223> OTHER INFORMATION: hairpin ribozyme

<400> SEQUENCE: 1
accuccccag aacccu                                                         16

<210> SEQ ID NO 2
<211> LENGTH: 16
<212> TYPE: RNA
<213> ORGANISM: homo sapiens
<220> FEATURE:
<221> NAME/KEY: misc_feature
<222> LOCATION: (1)...(16)
<223> OTHER INFORMATION: n = A,U,C or G

<400> SEQUENCE: 2
agggngucgg ggaggu                                                         16

<210> SEQ ID NO 3
<211> LENGTH: 16
<212> TYPE: RNA
<213> ORGANISM: Artificial Sequence
<220> FEATURE:
<223> OTHER INFORMATION: hairpin ribozyme

<400> SEQUENCE: 3
agaguguaag aaacua                                                         16

<210> SEQ ID NO 4
<211> LENGTH: 16
<212> TYPE: RNA
<213> ORGANISM: homo sapiens
<220> FEATURE:
<221> NAME/KEY: misc_feature
<222> LOCATION: (1)...(16)
<223> OTHER INFORMATION: n = A,U,C or G

<400> SEQUENCE: 4
uagungucua cacucu                                                         16

<210> SEQ ID NO 5
<211> LENGTH: 1664
<212> TYPE: DNA
<213> ORGANISM: homo sapiens
<220> FEATURE:
<221> NAME/KEY: CDS
<222> LOCATION: (103)...(1525)

<400> SEQUENCE: 5
gcctgatgtc gtcccacgcc gtgccggctc tcaggcgccg gaagtgagct gcgcacggcc         60
ggaagcggcg gacgcaggag gcctcgtgga ggacacagca gc atg gga cag tca          114
                                              Met Gly Gln Ser
                                                1 ggg agg tcc cgg cac cag aag cgc gcc ccg ccc cag gcg cag ctc cgc         162
Gly Arg Ser Arg His Gln Lys Arg Ala Pro Pro Gln Ala Gln Leu Arg
 5                  10                  15                  20 aac ctc gag gcc tat gcc gcg aac ccg cac tcg ttc gtg ttc acg cga         210
Asn Leu Glu Ala Tyr Ala Ala Asn Pro His Ser Phe Val Phe Thr Arg -continued

| | | | | | | | | | | | | | | | |
|---|---|---|---|---|---|---|---|---|---|---|---|---|---|---|---|
| | | | | 25 | | | | 30 | | | | 35 | | | |
| ggc | tgc | acg | ggt | cgc | aac | atc | cgg | cag | ctc | agc | ctg | gac | gtg | cgg | cgg | 258
| Gly | Cys | Thr | Gly | Arg | Asn | Ile | Arg | Gln | Leu | Ser | Leu | Asp | Val | Arg | Arg |
| | | | 40 | | | | | 45 | | | | 50 | | | |
| gtc | atg | gag | ccc | gtc | act | gcc | agc | cgt | ctg | cag | gtt | cgt | aag | aag | aac | 306
| Val | Met | Glu | Pro | Val | Thr | Ala | Ser | Arg | Leu | Gln | Val | Arg | Lys | Lys | Asn |
| | | | 55 | | | | | 60 | | | | | 65 | | |
| tcg | ctg | aag | gac | tgc | gtg | gca | gtg | gct | ggg | ccc | ctc | ggg | gtc | aca | cac | 354
| Ser | Leu | Lys | Asp | Cys | Val | Ala | Val | Ala | Gly | Pro | Leu | Gly | Val | Thr | His |
| | | 70 | | | | | 75 | | | | | 80 | | | |
| ttt | ctg | atc | cta | gca | aaa | caa | gag | acc | aat | gtc | tac | ttt | aag | ctg | atg | 402
| Phe | Leu | Ile | Leu | Ala | Lys | Gln | Glu | Thr | Asn | Val | Tyr | Phe | Lys | Leu | Met |
| 85 | | | | | 90 | | | | | 95 | | | | | 100 |
| cgc | ctc | cca | gga | ggc | ccc | acc | ttg | acc | ttc | cag | gtc | aag | aag | tac | tcg | 450
| Arg | Leu | Pro | Gly | Gly | Pro | Thr | Leu | Thr | Phe | Gln | Val | Lys | Lys | Tyr | Ser |
| | | | | 105 | | | | | 110 | | | | | 115 | |
| ctg | gtg | cgt | gat | gtg | gtc | tcc | tca | ctg | cgc | cgg | cac | cgc | atg | cac | gag | 498
| Leu | Val | Arg | Asp | Val | Val | Ser | Ser | Leu | Arg | Arg | His | Arg | Met | His | Glu |
| | | | 120 | | | | | 125 | | | | | 130 | | |
| cag | cag | ttt | gcc | cac | cca | ccc | ctc | ctg | gta | ctc | aac | agc | ttt | ggc | ccc | 546
| Gln | Gln | Phe | Ala | His | Pro | Pro | Leu | Leu | Val | Leu | Asn | Ser | Phe | Gly | Pro |
| | | 135 | | | | | 140 | | | | | 145 | | | |
| cat | ggt | atg | cat | gtg | aag | ctc | atg | gcc | acc | atg | ttc | cag | aac | ctg | ttc | 594
| His | Gly | Met | His | Val | Lys | Leu | Met | Ala | Thr | Met | Phe | Gln | Asn | Leu | Phe |
| | 150 | | | | | 155 | | | | | 160 | | | | |
| ccc | tcc | atc | aac | gtg | cac | aag | gtg | aac | ctg | aac | acc | atc | aag | cgc | tgc | 642
| Pro | Ser | Ile | Asn | Val | His | Lys | Val | Asn | Leu | Asn | Thr | Ile | Lys | Arg | Cys |
| 165 | | | | | 170 | | | | | 175 | | | | | 180 |
| ctc | ctc | atc | gac | tac | aac | ccc | gac | tcc | cag | gag | ctg | gac | ttc | cgc | cac | 690
| Leu | Leu | Ile | Asp | Tyr | Asn | Pro | Asp | Ser | Gln | Glu | Leu | Asp | Phe | Arg | His |
| | | | | 185 | | | | | 190 | | | | | 195 | |
| tat | agc | atc | aaa | gtt | gtt | cct | gtg | ggc | gcg | agt | cgc | ggg | atg | aag | aag | 738
| Tyr | Ser | Ile | Lys | Val | Val | Pro | Val | Gly | Ala | Ser | Arg | Gly | Met | Lys | Lys |
| | | | 200 | | | | | 205 | | | | | 210 | | |
| ctg | ctc | cag | gag | aag | ttc | ccc | aac | atg | agc | cgc | ctg | cag | gac | atc | agc | 786
| Leu | Leu | Gln | Glu | Lys | Phe | Pro | Asn | Met | Ser | Arg | Leu | Gln | Asp | Ile | Ser |
| | | 215 | | | | | 220 | | | | | 225 | | | |
| gag | ctg | ctg | gcc | acg | ggc | gcg | ggg | ctg | tcg | gag | agc | gag | gca | gag | cct | 834
| Glu | Leu | Leu | Ala | Thr | Gly | Ala | Gly | Leu | Ser | Glu | Ser | Glu | Ala | Glu | Pro |
| | 230 | | | | | 235 | | | | | 240 | | | | |
| gac | ggc | gac | cac | aac | atc | aca | gag | ctg | cct | cag | gct | gtc | gct | ggc | cgt | 882
| Asp | Gly | Asp | His | Asn | Ile | Thr | Glu | Leu | Pro | Gln | Ala | Val | Ala | Gly | Arg |
| 245 | | | | | 250 | | | | | 255 | | | | | 260 |
| ggc | aac | atg | cgg | gcc | cag | cag | agt | gca | gtg | cgg | ctc | acc | gag | atc | ggc | 930
| Gly | Asn | Met | Arg | Ala | Gln | Gln | Ser | Ala | Val | Arg | Leu | Thr | Glu | Ile | Gly |
| | | | | 265 | | | | | 270 | | | | | 275 | |
| ccg | cgg | atg | aca | ctg | cag | ctc | atc | aag | gtc | cag | gag | ggc | gtc | ggg | gag | 978
| Pro | Arg | Met | Thr | Leu | Gln | Leu | Ile | Lys | Val | Gln | Glu | Gly | Val | Gly | Glu |
| | | | 280 | | | | | 285 | | | | | 290 | | |
| ggc | aaa | gtg | atg | ttc | cac | agt | ttt | gtg | agc | aag | acg | gag | gag | gag | ctg | 1026
| Gly | Lys | Val | Met | Phe | His | Ser | Phe | Val | Ser | Lys | Thr | Glu | Glu | Glu | Leu |
| | | 295 | | | | | 300 | | | | | 305 | | | |
| cag | gcc | atc | ctg | gaa | gcc | aag | gag | aag | aag | ctg | cgg | ctg | aag | gct | cag | 1074
| Gln | Ala | Ile | Leu | Glu | Ala | Lys | Glu | Lys | Lys | Leu | Arg | Leu | Lys | Ala | Gln |
| | 310 | | | | | 315 | | | | | 320 | | | | |
| agg | cag | gcc | cag | cag | gcc | cag | aat | gtg | cag | cgc | aag | cag | gag | cag | cgg | 1122
| Arg | Gln | Ala | Gln | Gln | Ala | Gln | Asn | Val | Gln | Arg | Lys | Gln | Glu | Gln | Arg |
| 325 | | | | | 330 | | | | | 335 | | | | | 340 |
| gag | gcc | cac | aga | aag | aag | agc | ctg | gag | ggc | atg | aag | aag | gca | cgg | gtc | 1170

-continued

```
Glu Ala His Arg Lys Lys Ser Leu Glu Gly Met Lys Lys Ala Arg Val
            345                 350                 355 ggg ggt agt gat gaa gag gcc tct ggg atc cct tca agg acg gcg agc      1218
Gly Gly Ser Asp Glu Glu Ala Ser Gly Ile Pro Ser Arg Thr Ala Ser
        360                 365                 370 ctg gag ttg ggt gag gac gat gat gaa cag gaa gat gat gac atc gag      1266
Leu Glu Leu Gly Glu Asp Asp Asp Glu Gln Glu Asp Asp Asp Ile Glu
    375                 380                 385 tat ttc tgc cag gcg gtg ggc gag gcg ccc agt gag gac ctg ttc ccc      1314
Tyr Phe Cys Gln Ala Val Gly Glu Ala Pro Ser Glu Asp Leu Phe Pro
390                 395                 400 gag gcc aag cag aaa cgg ctt gcc aag tct cca ggg cgg aag cgg aag      1362
Glu Ala Lys Gln Lys Arg Leu Ala Lys Ser Pro Gly Arg Lys Arg Lys
405                 410                 415                 420 cgg tgg gaa atg gat cga ggc agg ggt cgc ctt tgt gac cag aag ttt      1410
Arg Trp Glu Met Asp Arg Gly Arg Gly Arg Leu Cys Asp Gln Lys Phe
                425                 430                 435 ccc aag acc aag gac aag tcc cag gga gcc cag gcc agg cgg ggg ccc      1458
Pro Lys Thr Lys Asp Lys Ser Gln Gly Ala Gln Ala Arg Arg Gly Pro
            440                 445                 450 aga ggg gct tcc cgg gat ggt ggg cga ggc cgg ggc cga ggc cgc cca      1506
Arg Gly Ala Ser Arg Asp Gly Gly Arg Gly Arg Gly Arg Gly Arg Pro
        455                 460                 465 ggg aag aga gtg gcc tga g cccaagccgc accggagcag cggctggatt          1555
Gly Lys Arg Val Ala *
    470 gaacgcccca gattgggccc cgagatgtgg ccctcggttt cctttcataa aggagttgtg    1615 tccccagccc ttccactcca gtaaagaact gaattggcaa aaaaaaaaa                1664
```

<210> SEQ ID NO 6
<211> LENGTH: 473
<212> TYPE: PRT
<213> ORGANISM: homo sapiens

<400> SEQUENCE: 6

```
Met Gly Gln Ser Gly Arg Ser Arg His Gln Lys Arg Ala Pro Pro Gln
1               5                   10                  15

Ala Gln Leu Arg Asn Leu Glu Ala Tyr Ala Ala Asn Pro His Ser Phe
            20                  25                  30

Val Phe Thr Arg Gly Cys Thr Gly Arg Asn Ile Arg Gln Leu Ser Leu
        35                  40                  45

Asp Val Arg Arg Val Met Glu Pro Val Thr Ala Ser Arg Leu Gln Val
    50                  55                  60

Arg Lys Lys Asn Ser Leu Lys Asp Cys Val Ala Val Ala Gly Pro Leu
65                  70                  75                  80

Gly Val Thr His Phe Leu Ile Leu Ala Lys Gln Glu Thr Asn Val Tyr
                85                  90                  95

Phe Lys Leu Met Arg Leu Pro Gly Gly Pro Thr Leu Thr Phe Gln Val
            100                 105                 110

Lys Lys Tyr Ser Leu Val Arg Asp Val Val Ser Ser Leu Arg Arg His
        115                 120                 125

Arg Met His Glu Gln Gln Phe Ala His Pro Pro Leu Leu Val Leu Asn
    130                 135                 140

Ser Phe Gly Pro His Gly Met His Val Lys Leu Met Ala Thr Met Phe
145                 150                 155                 160

Gln Asn Leu Phe Pro Ser Ile Asn Val His Lys Val Asn Leu Asn Thr
                165                 170                 175
```

```
Ile Lys Arg Cys Leu Leu Ile Asp Tyr Asn Pro Asp Ser Gln Glu Leu
            180                 185                 190
Asp Phe Arg His Tyr Ser Ile Lys Val Val Pro Val Gly Ala Ser Arg
        195                 200                 205
Gly Met Lys Lys Leu Leu Gln Glu Lys Phe Pro Asn Met Ser Arg Leu
    210                 215                 220
Gln Asp Ile Ser Glu Leu Leu Ala Thr Gly Ala Gly Leu Ser Glu Ser
225                 230                 235                 240
Glu Ala Glu Pro Asp Gly Asp His Asn Ile Thr Glu Leu Pro Gln Ala
                245                 250                 255
Val Ala Gly Arg Gly Asn Met Arg Ala Gln Gln Ser Ala Val Arg Leu
            260                 265                 270
Thr Glu Ile Gly Pro Arg Met Thr Leu Gln Leu Ile Lys Val Gln Glu
        275                 280                 285
Gly Val Gly Glu Gly Lys Val Met Phe His Ser Phe Val Ser Lys Thr
    290                 295                 300
Glu Glu Glu Leu Gln Ala Ile Leu Glu Ala Lys Glu Lys Lys Leu Arg
305                 310                 315                 320
Leu Lys Ala Gln Arg Gln Ala Gln Gln Ala Gln Asn Val Gln Arg Lys
                325                 330                 335
Gln Glu Gln Arg Glu Ala His Arg Lys Lys Ser Leu Glu Gly Met Lys
            340                 345                 350
Lys Ala Arg Val Gly Gly Ser Asp Glu Glu Ala Ser Gly Ile Pro Ser
        355                 360                 365
Arg Thr Ala Ser Leu Glu Leu Gly Glu Asp Asp Glu Gln Glu Asp
    370                 375                 380
Asp Asp Ile Glu Tyr Phe Cys Gln Ala Val Gly Glu Ala Pro Ser Glu
385                 390                 395                 400
Asp Leu Phe Pro Glu Ala Lys Gln Lys Arg Leu Ala Lys Ser Pro Gly
                405                 410                 415
Arg Lys Arg Lys Arg Trp Glu Met Asp Arg Gly Arg Gly Arg Leu Cys
            420                 425                 430
Asp Gln Lys Phe Pro Lys Thr Lys Asp Lys Ser Gln Gly Ala Gln Ala
        435                 440                 445
Arg Arg Gly Pro Arg Gly Ala Ser Arg Asp Gly Arg Gly Arg Gly
    450                 455                 460
Arg Gly Arg Pro Gly Lys Arg Val Ala
465                 470

<210> SEQ ID NO 7
<211> LENGTH: 87
<212> TYPE: DNA
<213> ORGANISM: Artificial Sequence
<220> FEATURE:
<223> OTHER INFORMATION: synthetic oligonucleotides
<221> NAME/KEY: misc_feature
<222> LOCATION: (1)...(87)
<223> OTHER INFORMATION: n = A,T,C or G

<400> SEQUENCE: 7
cgcgtaccag gtaatatacc acggaccgaa gtccgtgtgt ttctctggtn nnnttctnnn    60
nnnnnggatc ctgtttccgc ccggttt                                       87

<210> SEQ ID NO 8
<211> LENGTH: 22
<212> TYPE: DNA
```

```
<213> ORGANISM: Artificial Sequence
<220> FEATURE:
<223> OTHER INFORMATION: synthetic oligonucleotide

<400> SEQUENCE: 8
gtccgtggta tattacctgg ta                                              22

<210> SEQ ID NO 9
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 9
cgaaaccggg cggaaacagg                                                 20

<210> SEQ ID NO 10
<211> LENGTH: 52
<212> TYPE: RNA
<213> ORGANISM: Artificial Sequence
<220> FEATURE:
<223> OTHER INFORMATION: hairpin ribozyme
<221> NAME/KEY: misc_feature
<222> LOCATION: (1)...(52)
<223> OTHER INFORMATION: n = A,U,C or G

<400> SEQUENCE: 10
nnnnnnnnag aannnnacca gagaaacaca cguuguggua uauuaccugg ua             52

<210> SEQ ID NO 11
<211> LENGTH: 27
<212> TYPE: DNA
<213> ORGANISM: homo sapiens

<400> SEQUENCE: 11
ccatcctaat acgactcact atagggc                                         27

<210> SEQ ID NO 12
<211> LENGTH: 43
<212> TYPE: DNA
<213> ORGANISM: homo sapiens
<220> FEATURE:
<221> NAME/KEY: misc_feature
<222> LOCATION: (1)...(42)
<223> OTHER INFORMATION: n = A,T,C or G

<400> SEQUENCE: 12
cgatgctcct ctagactcga gggtaccacc tccccgacnc cct                       43

<210> SEQ ID NO 13
<211> LENGTH: 38
<212> TYPE: DNA
<213> ORGANISM: Artificial Sequence
<220> FEATURE:
<223> OTHER INFORMATION: primer

<400> SEQUENCE: 13
ggccacgcgt cgactagtac tttttttttt tttttttv                             38

<210> SEQ ID NO 14
<211> LENGTH: 20
<212> TYPE: DNA
<213> ORGANISM: homo sapiens

<400> SEQUENCE: 14
```

-continued cggctcaccg agatcggccc 20

<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
ggccacgcgt cgactagtac t 21

<210> SEQ ID NO 16
<211> LENGTH: 429
<212> TYPE: PRT
<213> ORGANISM: mus musculus

<400> SEQUENCE: 16

```
Met Gly Gln Ser Gly Arg Ser Arg His Gln Lys Arg Asn Arg Ala Gln
 1               5                  10                  15

Ala Gln Leu Arg Asn Leu Glu Ser Tyr Ala Ala Gln Pro His Ser Phe
            20                  25                  30

Val Phe Thr Arg Gly Arg Ala Gly Arg Asn Val Arg Gln Leu Ser Leu
        35                  40                  45

Asp Val Arg Arg Val Met Glu Pro Leu Thr Ala Thr Arg Leu Gln Val
    50                  55                  60

Arg Lys Lys Asn Ser Leu Lys Asp Cys Val Ala Val Ala Gly Pro Leu
65                  70                  75                  80

Gly Val Thr His Phe Leu Ile Leu Thr Lys Thr Cys Asn Ser Val Tyr
                85                  90                  95

Leu Lys Leu Met Arg Leu Pro Gly Gly Pro Thr Leu Thr Phe Gln Ile
            100                 105                 110

Ser Lys Tyr Thr Leu Ile Arg Asp Val Val Ser Ser Leu Arg Arg His
        115                 120                 125

Arg Met His Glu Gln Gln Phe Asn His Pro Leu Leu Val Leu Asn
    130                 135                 140

Ser Phe Gly Pro Gln Ala Met His Ile Lys Leu Met Ala Thr Met Phe
145                 150                 155                 160

Gln Asn Leu Phe Pro Ser Ile Asn Val His Thr Val Asn Leu Asn Thr
                165                 170                 175

Ile Lys Arg Cys Leu Leu Ile Asn Tyr Asn Pro Asp Ser Gln Glu Leu
            180                 185                 190

Asp Phe Arg His Tyr Ser Val Lys Val Pro Val Gly Ala Ser Arg
        195                 200                 205

Gly Met Lys Lys Leu Leu Gln Glu Lys Phe Pro Asn Met Ser Arg Leu
    210                 215                 220

Gln Asp Ile Ser Glu Leu Leu Ala Thr Gly Val Gly Leu Ser Asp Ser
225                 230                 235                 240

Glu Val Glu Pro Asp Gly Glu His Asn Thr Thr Glu Leu Pro Gln Ala
                245                 250                 255

Val Ala Gly Arg Gly Asn Met Gln Ala Gln Ser Ala Val Arg Leu
            260                 265                 270

Thr Glu Ile Gly Pro Arg Met Thr Leu Gln Leu Ile Lys Ile Gln Glu
        275                 280                 285

Gly Val Gly Asn Gly Asn Val Leu Phe His Ser Phe Val His Lys Thr
    290                 295                 300
```

```
Glu Glu Glu Leu Gln Ala Ile Leu Ala Ala Lys Glu Lys Leu Arg
305                 310                 315                 320

Leu Lys Ala Gln Arg Gln Asn Gln Gln Ala Glu Asn Leu Gln Phe Ser
                325                 330                 335

Arg Ser Cys Arg Gly Pro Gln Glu Glu Pro Gly Arg His Lys Ala
            340                 345                 350

Ser Pro Cys Lys Gly Arg Arg Glx Gln Glx Cys Glx Gly Pro Arg Gly
            355                 360                 365

Thr Ala Arg Gly Gln Trp Gly Ala Gly Gln Pro Glu Asp Glu Glu Asp
            370                 375                 380

Asp Ala Glu Tyr Phe Arg Gln Ala Val Gly Glu Pro Asp Glu Asp
385                 390                 395                 400

Leu Phe Pro Thr Ala Ala Lys Arg Arg Gln Gly Gly Leu Leu Ala
                405                 410                 415

Lys Lys Gln Arg Gly Phe Glu Gln Arg Pro Gly Asn Lys
                420                 425

<210> SEQ ID NO 17
<211> LENGTH: 460
<212> TYPE: PRT
<213> ORGANISM: Drosophila

<400> SEQUENCE: 17

Met Gly Gly Lys Lys Val His Pro Lys Thr Arg Thr Ala Ala Phe
1               5                   10                  15

Lys Ala Ser Glu Pro Ser Glu Ile Val Glu Ala Pro His Ser Phe Val
                20                  25                  30

Ile His Arg Gly Leu Ala Cys Pro Tyr Ile Thr Asp Leu Thr Leu Asp
            35                  40                  45

Phe Arg Arg Ile Met Glu Pro Phe Thr Ala Ser Asn Leu Arg Glu Lys
        50                  55                  60

Arg Met Asn Arg Ile Gln Asp Phe Val Cys Leu Ser Ser Phe Phe His
65                  70                  75                  80

Val Ser His Met Gly Ile Phe Asn Lys Ala Ser Ile Gln Leu Ser Phe
                85                  90                  95

Lys Val Val Arg Leu Pro Arg Gly Pro Ser Leu Thr Phe Lys Val His
                100                 105                 110

Gln Phe Thr Leu Ala Arg Asp Val Ile Ser Leu Ser Lys Lys Gln Met
            115                 120                 125

Ile Asp Asn Asp His Phe Lys His Ala Pro Leu Val Ile Met Asn Asn
            130                 135                 140

Phe Ser Gly Asp Gly Lys His Leu Lys Leu Met Ala Thr Thr Phe Gln
145                 150                 155                 160

Asn Met Phe Pro Ser Ile Asn Leu Ala Thr Val Asn Ile Gly Thr Ile
                165                 170                 175

Arg Arg Cys Val Leu Phe Ser Tyr Asn Pro Asp Thr Lys Leu Val Glu
            180                 185                 190

Met Arg His Tyr Ser Val Gln Val Pro Val Gly Leu Lys Arg Ala
            195                 200                 205

Val Gln Lys Ile Val Lys Gly Thr Val Pro Asn Leu Gly Lys Cys Asn
    210                 215                 220

Glu Val Val Asp Phe Val Thr Lys Asp Gly Tyr Ala Ser Glu Ser Glu
225                 230                 235                 240

Ala Glu Asp Asp Glu Gln Ser His Val Val Leu Ala Gln Thr Leu Lys
                245                 250                 255
```

-continued

```
Ser Lys Gly Asn Leu Glu Asp Lys Lys Ser Ser Ile Lys Leu His Glu
            260                 265                 270

Ile Gly Pro Arg Leu Thr Met Gln Leu Ile Lys Ile Glu Glu Gly Leu
        275                 280                 285

Leu Thr Gly Glu Val Leu Tyr His Cys His Val Val Lys Thr Glu Asp
    290                 295                 300

Glu Lys Glu Thr Leu Arg Lys Leu Val Glu Lys Arg Lys Gln Lys
305                 310                 315                 320

Glu Gln Arg Lys Lys Glu Gln Ala Glu Asn Arg Ala Phe Asn Leu Lys
                325                 330                 335

Leu Lys Lys Asp Glu Lys Trp Ala Ala Lys Arg Ala Ala Glu Gly Arg
            340                 345                 350

Thr Asp Ser Asp Pro Glu Asp Ala Glu Tyr Tyr Lys Glu Glu Val
        355                 360                 365

Gly Glu Glu Pro Asp Glu Glu Leu Phe Lys Met Glu Ala Lys Ser Ser
    370                 375                 380

Arg Lys Arg Pro Ser Leu Gly Gly Met Lys Tyr Lys Asn Lys Arg
385                 390                 395                 400

Ala Lys Leu Asp Thr Lys Asp Lys Asn Asp Lys Ser Glu Arg Thr Asp
                405                 410                 415

Phe Tyr Asp Arg Lys Cys Lys Phe Asp Arg Lys Asp Lys Asp Lys
            420                 425                 430

Phe Asp Pro Lys Asn Gly Arg Ala Lys Phe Asp Pro Lys Asn Lys Arg
        435                 440                 445

Ala Lys Phe Asp His Pro Lys Ser Arg Lys Ser Lys
    450                 455                 460
```

<210> SEQ ID NO 18
<211> LENGTH: 15
<212> TYPE: DNA
<213> ORGANISM: homo sapiens

<400> SEQUENCE: 18
agggcgtcgg ggagg                                                  15

<210> SEQ ID NO 19
<211> LENGTH: 358
<212> TYPE: PRT
<213> ORGANISM: mus musulus
<220> FEATURE:
<221> NAME/KEY: VARIANT
<222> LOCATION: (1)...(358)
<223> OTHER INFORMATION: Xaa = Any Amino Acid

<400> SEQUENCE: 19

```
Phe Gly Gln Gly Gly Lys Gln Ala Ala Trp Gly Ser Pro Gly Gly Pro
1               5                   10                  15

Asp Ile Arg Ser Ala Ile Ala Pro Gly Glu Leu Arg Asn Leu Glu Ser
            20                  25                  30

Tyr Ala Ala Gln Pro His Ser Phe Val Phe Thr Arg Gly Arg Ala Gly
        35                  40                  45

Arg Asn Val Arg Gln Leu Ser Leu Asp Val Arg Arg Val Met Glu Pro
    50                  55                  60

Leu Thr Ala Thr Arg Leu Gln Val Arg Lys Lys Asn Ser Leu Lys Asp
65                  70                  75                  80

Cys Val Ala Val Ala Gly Pro Leu Gly Val Thr His Phe Leu Ile Leu
                85                  90                  95
```

```
Thr Lys Thr Asp Asn Ser Val Tyr Leu Lys Leu Met Arg Leu Pro Gly
            100                 105                 110
Gly Pro Thr Leu Thr Phe Gln Ile Ser Lys Tyr Thr Leu Ile Arg Asp
        115                 120                 125
Val Val Ser Ser Leu Arg Arg His Arg Met His Glu Gln Gln Phe Asn
    130                 135                 140
His Pro Pro Leu Leu Val Leu Asn Ser Phe Gly Pro Gln Gly Met His
145                 150                 155                 160
Ile Lys Leu Met Ala Thr Met Phe Gln Asn Leu Phe Pro Ser Ile Asn
                165                 170                 175
Val His Thr Val Asn Leu Asn Thr Ile Lys Arg Cys Leu Leu Ile Asn
            180                 185                 190
Tyr Asn Pro Asp Ser Gln Glu Leu Asp Phe Arg His Tyr Ser Val Lys
        195                 200                 205
Val Val Pro Val Gly Ala Ser Arg Gly Met Lys Lys Leu Leu Gln Glu
    210                 215                 220
Lys Phe Pro Asn Met Ser Arg Leu Gln Asp Ile Ser Glu Leu Leu Ala
225                 230                 235                 240
Thr Gly Val Gly Leu Ser Asp Ser Glu Val Glu Pro Asp Gly Glu His
                245                 250                 255
Asn Thr Thr Glu Leu Pro Gln Ala Val Ala Gly Arg Gly Asn Met Gln
            260                 265                 270
Ala Gln Gln Ser Ala Val Arg Leu Thr Glu Ile Gly Pro Arg Met Thr
        275                 280                 285
Leu Gln Leu Ile Lys Ile Gln Glu Gly Val Gly Asn Gly Asn Val Leu
    290                 295                 300
Phe His Ser Phe Val His Lys Thr Glu Glu Leu Gln Ala Ile Leu
305                 310                 315                 320
Ala Ala Lys Glu Glu Lys Leu Arg Leu Lys Ala Gln Arg Gln Asn Gln
                325                 330                 335
Gln Ala Glu Asn Leu Gln Arg Xaa Arg Ser Cys Arg Xaa Pro Thr Arg
            340                 345                 350
Arg Arg Ala Trp Gln Ala
        355

<210> SEQ ID NO 20
<211> LENGTH: 137
<212> TYPE: PRT
<213> ORGANISM: homo sapiens
<220> FEATURE:
<221> NAME/KEY: VARIANT
<222> LOCATION: (1)...(137)
<223> OTHER INFORMATION: Xaa = Any Amino Acid

<400> SEQUENCE: 20

Leu Gly Pro Arg Val Thr His Phe Leu Ile Leu Ser Lys Thr Glu Thr
1               5                   10                  15
Asn Val Tyr Phe Lys Leu Met Arg Leu Pro Gly Gly Pro Thr Leu Thr
            20                  25                  30
Phe Gly Val Lys Lys Tyr Ser Leu Val Arg Asp Val Ser Ser Leu
        35                  40                  45
Arg Arg His Arg Met His Glu Gln Gln Phe Ala His Pro Pro Leu Leu
    50                  55                  60
Val Leu Asn Ser Phe Gly Pro His Gly Met His Val Lys Leu Met Ala
65                  70                  75                  80
```

-continued

```
Thr Met Phe Gln Asn Leu Phe Pro Ser Ile Asn Val His Lys Val Asn
                85                  90                  95

Leu Asn Thr Ile Lys Arg Cys Ser Ser Xaa Asp Leu Lys Pro Gly Phe
            100                 105                 110

Pro Arg Ser Leu Asp Phe Arg Pro Ile Ile Ala Phe Lys Gly Gly Ser
        115                 120                 125

Cys Trp Ala Pro Asn Ser Gly Gly Leu
    130                 135
```